(12) United States Patent
Patou

(10) Patent No.: US 10,993,984 B2
(45) Date of Patent: May 4, 2021

(54) TERLIPRESSIN COMPOSITIONS AND THEIR METHODS OF USE

(71) Applicant: Chiasma, Inc., Waltham, MA (US)

(72) Inventor: Gary Patou, Los Altos Hills, CA (US)

(73) Assignee: Chiasma, Inc., Needham, MA (US)

( * ) Notice: Subject to any disclaimer, the term of this patent is extended or adjusted under 35 U.S.C. 154(b) by 0 days.

(21) Appl. No.: 16/343,232

(22) PCT Filed: Oct. 20, 2017

(86) PCT No.: PCT/US2017/057601
§ 371 (c)(1),
(2) Date: Apr. 18, 2019

(87) PCT Pub. No.: WO2018/075897
PCT Pub. Date: Apr. 26, 2018

(65) Prior Publication Data
US 2019/0240284 A1    Aug. 8, 2019

Related U.S. Application Data

(60) Provisional application No. 62/472,291, filed on Mar. 16, 2017, provisional application No. 62/410,971, filed on Oct. 21, 2016.

(51) Int. Cl.
| | |
|---|---|
| *A61P 9/02* | (2006.01) |
| *A61K 38/095* | (2019.01) |
| *A61P 1/16* | (2006.01) |
| *A61P 9/12* | (2006.01) |
| *A61K 9/28* | (2006.01) |
| *A61K 9/48* | (2006.01) |
| *A61K 31/573* | (2006.01) |
| *A61K 45/06* | (2006.01) |

(52) U.S. Cl.
CPC .............. *A61K 38/095* (2019.01); *A61K 9/28* (2013.01); *A61K 9/4891* (2013.01); *A61K 31/573* (2013.01); *A61K 45/06* (2013.01); *A61P 1/16* (2018.01); *A61P 9/02* (2018.01); *A61P 9/12* (2018.01)

(58) Field of Classification Search
CPC ...... A61K 38/095; A61K 9/28; A61K 9/4891; A61K 31/573; A61K 45/06; A61K 31/4425; A61K 31/451; A61K 38/1816; A61K 31/165; A61P 1/16; A61P 9/02; A61P 9/12
See application file for complete search history.

(56) References Cited

U.S. PATENT DOCUMENTS

| | | |
|---|---|---|
| 3,558,590 A | 1/1971 | Cort et al. |
| 7,160,853 B2 | 1/2007 | Lebrec et al. |
| 8,778,881 B2 | 7/2014 | Wisniewski et al. |
| 8,883,965 B2 | 11/2014 | Wisniewski et al. |
| 9,655,945 B2 | 5/2017 | Angeli et al. |
| 10,335,452 B2 | 7/2019 | Jamil et al. |
| 2011/0257095 A1* | 10/2011 | Salama ................ A61K 9/0031 514/10.9 |
| 2015/0307578 A1 | 10/2015 | Castillo et al. |
| 2016/0113994 A1 | 4/2016 | Jamil et al. |
| 2016/0158159 A1 | 6/2016 | Mamluk et al. |
| 2017/0000844 A1 | 1/2017 | Angeli et al. |
| 2018/0042987 A1 | 2/2018 | Klotz et al. |
| 2019/0125992 A1 | 5/2019 | Hafner |

FOREIGN PATENT DOCUMENTS

| | | |
|---|---|---|
| AU | 2015201581 A1 | 4/2015 |
| EP | 1188443 A1 | 3/2002 |
| GB | 2478849 A | 9/2011 |
| WO | 2015013690 A1 | 1/2015 |
| WO | 2016065117 A1 | 4/2016 |

OTHER PUBLICATIONS

Rittig et al (Movement Disorders, 1991, vol. 6, No. 1, 21-28) (Year: 1991).*
Bieker (World J Gastroenterol, Mar. 14, 2011, 17(10):1237-1248) (Year: 2011).*
Bieker (World J Gastroenterol, Aug. 21, 2013, 19(31), 5035-5050) (Year: 2013).*
Chobanian et al (The New England Journal of Medicine, 1979, 301, 68-73) (Year: 1979).*
Angeli. "Terlipressin for Hepatorenal Syndrome: Novel Strategies and Future Perspectives," Front Gastrointest. Res., 2011, 28:189-197.
Annamalai et al. "Management of refractory ascites in cirrhosis: Are we out of date?" World Journal of Hepatology, 2016, 8(28):1182-119.
Arroyo et al. "Ascites and hepatorenal syndrome in cirrhosis: pathophysiological basis of therapy and current management," Journal of Hepatology, 2003, 38:S69-S89.
Biecker. "Gastrointestinal Bleeding in Cirrhotic Patients with Portal Hypertension," ISRN Hepatology, 2013, 2013:1-20.
Cassidy et al. "Nonalcoholic steatohepatitis (NASH) drugs market," Nature Reviews, 2016, 15(1):745-746.
Consumer Medicine Information for LUCASSIN® Terlipressin 0.85 mg powder for injection, MIMS, 2018, 1-2.
De Vries et al. "Management of cholestatic disease in 2017," Liver International, 2017, 37(1):123-129.

(Continued)

*Primary Examiner* — Sudhakar Katakam
(74) *Attorney, Agent, or Firm* — Goodwinlaw.com

(57) ABSTRACT

Methods are disclosed of treating or preventing hypotension (e.g., neurogenic orthostatic hypotension or postprandial hypotension) or portal hypertension (e.g., bleeding esophageal varices associated with portal hypertension) or ascites (e.g., ascites associated with liver cirrhosis), by oral administration to affected subjects of compositions comprising a therapeutically effective amount of terlipressin or a pharmaceutically acceptable salt thereof.

13 Claims, 1 Drawing Sheet

(56) References Cited

OTHER PUBLICATIONS

Extended European Search Report for European Application No. 17862085 dated Jun. 3, 2020.
Filozof et al. "Non-alcoholic steatohepatitis: limited available treatment options but promising drugs in development and recent progress towards a regulatory approval pathway," Drugs, 2015, 75:1373-1392.
Franceschet et al. "Therapeutic approaches for portal biliopathy: A systematic review," World J Gastroenterol, 2016, 22(45): 9909-9920.
Frith et al. "New horizons in orthostatic hypotension," Age and Ageig, 2017, 46(2): 168-174.
Gluud et al. "Terlipressin for hepatorenal syndrome (Review)," The Cochrane Library, 2012, 9:1-35.
Habib et al. "Vasopressin V2-receptor antagonists in patients with cirrhosis, ascites and hyponatremia," Ther. Adv. Gastroenterol., 2012, 5(3): 189-197.
Hakusui et al. "Postprandial hypotension: microneurographic analysis and treatment with vasopressin," Neurology, 1991,41:712-715.
He et al. "A Selective V1a Receptor Agonist, Selepressin, Is Superior to Arginine Vasopressin and to Norepinephrine in Ovine Septic Shock," Crit. Care Med., 2016, 44(1):23-31.
International Search Report for PCT/US2017/57601 dated Jan. 9, 2018.
Iaacson, "Managed care approach to the treatment of neurogenic orthostatic hypotension," The American Journal of Managed Care, 2015, 21(13): s258-s268.
Krag et al. "Terlipressin Improves Renal Function in Patients with Cirrhosis and Ascites Without Hepatorenal Syndrome," Hepatology, 2007, 46(6):1863-1871.
Lisk. "Postprandial hypotension," GM Journal, 2010, 42:203-206.
Lubart. "Postprandial Hypotension in Long-Term Care Elderly Patients on Enteral Feeding," JAGS, 2006, 54:1377-1381.
Manning et al. "Oxytocin and Vasopressin Agonists and Antagonists as Research Tools and Potential Therapeutics," Journal of Neuroendocrinology, 2012, 24:609-628.
Moreau et al. "Comparison of the effect of terlipressin and albumin on arterial blood volume in patients with cirrhosis and tense ascites treated by paracentesis: a randomised pilot study," Gut, 2002, 50:90-94.
Nusrat et al. "Cirrhosis and its complications: Evidence based treatment," World J. Gastroenterol., 2014, 20(18):5442-5460.
Ong et al. "Pharmacological Treatment of Post-Prandial Reductions in Blood Pressure: a systematic review," JAGS, 2014,62(4):1-52.
Product information for AusPAR Glypressin, Ferring Pharmaceuticals Pty Ltd, 2012, 1-18.
Trahair et al. "Postprandial Hypotension: A Systematic Review," JAMDA, 2014, 15:394-409.
Wong. "Treatment of hepatorenal syndrome," Indian Journal of Gastroenterology, 2006, 25(1):S8-S12.

* cited by examiner

FIG 1A/ IV Terlipressin, 0.2 mg
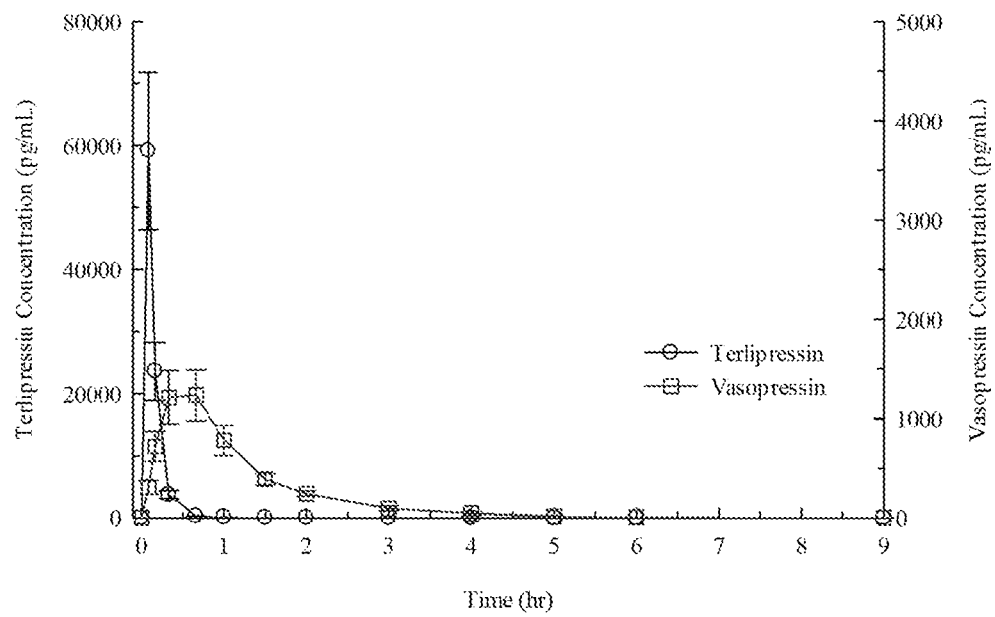
FIG 1B/ Oral Terlipressin, 20 mg
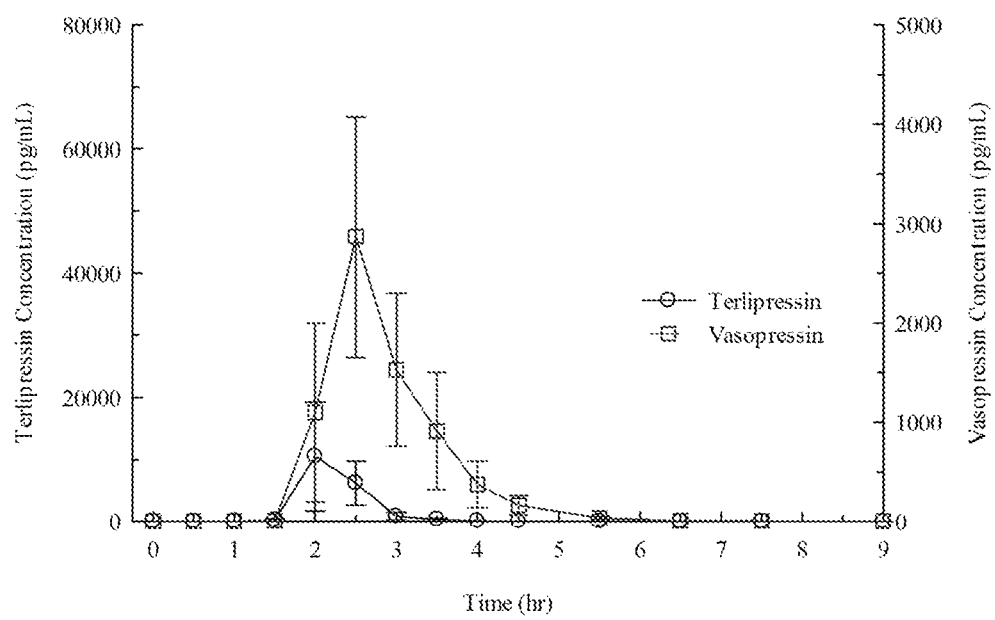

TERLIPRESSIN COMPOSITIONS AND THEIR METHODS OF USE

CROSS REFERENCE TO RELATED APPLICATIONS

This application claims the benefit and priority to U.S. Provisional Patent Application No. 62/410,971 filed Oct. 21, 2016, and U.S. Provisional Patent Application No. 62/472,291 filed Mar. 16, 2017, each of which is hereby incorporated by reference herein in its entirety.

FIELD OF THE TECHNOLOGY

The present invention relates generally to compositions and methods for treating a subject suffering from hypotension (e.g., neurogenic orthostatic hypotension or postprandial hypotension), portal hypertension (e.g., bleeding esophageal varices associated with portal hypertension) or ascites (e.g., ascites associated with liver cirrhosis) comprising orally administering pharmaceutical compositions of terlipressin.

BACKGROUND

Techniques enabling efficient transfer of a substance of interest across a biological barrier are of considerable interest in the fields of biotechnology and medicine. For example, such techniques may be used for the transport of a variety of different substances across a biological barrier regulated by tight junctions (i.e., the mucosal epithelia, which include the intestinal and respiratory epithelia, and the vascular endothelia, which include the blood-brain barrier, nasal membrane, cornea and other eye membranes, and genito-urinary membranes). In particular, there is great interest in oral delivery of therapeutic agents to avoid the use of more invasive means of administration and hence improve patient convenience and compliance.

Terlipressin is an analog of vasopressin and has been used, administered intravenously, for example for treatment of esophageal varices, septic shock, hepatorenal syndrome, and in the management of low blood pressure. A need exists for an efficient, specific, non-invasive, low-risk means for the non-invasive delivery of therapeutic agents such as terlipressin.

SUMMARY

Described herein are certain orally available compositions comprising terlipressin, oral dosage forms comprising terlipressin, and related methods of use, for example for treating neurogenic orthostatic hypotension, portal hypertension (e.g., bleeding esophageal varices associated with portal hypertension) or ascites (e.g. ascites associated with liver cirrhosis). In some embodiments, terlipressin exhibits improved bioavailability (BA) in a composition or oral dosage form described herein relative to terlipressin configured in another formulation or dosage form. In particular, terlipressin exhibits improved oral bioavailability in a composition or oral dosage form described herein, for example, relative to composition substantially free of the medium chain fatty acid salt component described herein or having a lower amount of the medium chain fatty acid salt component described herein. Such improvement in relative BA (e.g., oral BA) may be on the order of at least about 1.5-, 2-, 3-, 5-, 10- or 20-fold. In some embodiments, oral terlipressin has a BA of at least 1% or 2% or more.

In some embodiments, the methods described herein provide about 1 to about 1000 µg/mL terlipressin concentration in a subject. In some embodiments, the methods described herein provide about 10 to about 600 µg/mL terlipressin concentration in a subject, e.g., in the plasma of the subject. In some embodiments, the methods described herein provide about 20 to about 200 µg/mL terlipressin concentration in a subject. In some embodiments, the methods described herein provide about 60 µg/mL terlipressin concentration in a subject.

In some embodiments, the methods described herein provide about 1 to about 200 µg/mL (lysine-) vasopressin concentration in a subject. (Vasopressin is the active metabolite of terlipressin.) In some embodiments, the methods described herein provide about 2 to about 100 µg/mL vasopressin concentration in a subject, e.g., in the plasma of the subject. In some embodiments, the methods described herein provide about 3 to about 30 µg/mL vasopressin concentration in a subject. In some embodiments, the methods described herein provide about 10 µg/mL vasopressin concentration in a subject In an aspect, provided is a method of treating a subject suffering from hypotension (e.g., neurogenic orthostatic hypotension or postprandial hypotension), the method comprising orally administering a pharmaceutical composition (e.g., solid dosage composition, oral dosage form) configured as a tablet or capsule comprising a therapeutically effective amount (e.g., at least 5 mg (e.g., 5, 7, 10, 15, 17, 20, 25, 30 mg)) of terlipressin or a pharmaceutically acceptable salt thereof, 1, 2, 3, or 4 times daily, thereby treating the subject.

In some embodiments, the tablet or capsule is administered 1 or 2 times daily. In some embodiments the tablet or capsule is administered 2 times daily. In some embodiments the tablet or capsule is administered 4 times daily. In some embodiments the tablet or capsule is administered 3 times daily. In some embodiments, the tablet or capsule comprises 5 to 30 mg terlipressin. In some embodiments, the tablet or capsule comprises about 10 to about 30 mg terlipressin (e.g., about 15 to about 25 mg, about 18 to about 22 mg terlipressin). In some embodiments, the tablet or capsule comprises at least 5 mg (e.g., 5, 7, 10, 15, 17, 20, 25, 30 mg).

In some embodiments, the tablet or capsule comprises 20 mg terlipressin.

In some embodiments, the subject is administered 5 to 100 mg terlipressin daily (e.g., 20 to 100 mg terlipressin daily, 40 to 100 mg terlipressin daily, 60 to 100 mg terlipressin daily, e.g., 80 mg terlipressin daily).

In some embodiments, multiple tablets or capsules are administered 2 times daily. In some embodiments, multiple tablets or capsules are administered 3 times daily.

In some embodiments, the subject is administered at least 10, 20, 30, 40, 50, 60 mg terlipressin daily.

In some embodiments, the method results in reduced side effects relative to a method of administering terlipressin by other forms of administration (e.g., intravenous administration).

In some embodiments, the method provides greater patient compliance (e.g., compliance by a subject described herein) relative to a method of administering terlipressin by other forms of administration (e.g., intravenous administration).

In an aspect, provided is a method of treating a subject suffering from portal hypertension (e.g., bleeding esophageal varices associated with portal hypertension), the method comprising orally administering a pharmaceutical composition (e.g., solid dosage composition, oral dosage form) configured as a tablet or capsule comprising a therapeutically effective amount (e.g., at least 5 mg (e.g., 5, 7, 10, 15, 17, 20, 25, 30 mg)) of terlipressin or a pharmaceutically acceptable salt thereof, 1, 2, 3, or 4 times daily, thereby treating the subject.

In some embodiments, the tablet or capsule is administered 1 to 4 times daily. In some embodiments, the tablet or capsule is administered 1 or 2 times daily. In some embodiments the tablet or capsule is administered 2 times daily. In some embodiments the tablet or capsule is administered 4 times daily. In some embodiments the tablet or capsule is administered 3 times daily.

In some embodiments, the tablet or capsule comprises 5 to 30 mg terlipressin. In some embodiments, the tablet or capsule comprises 10 to 30 mg terlipressin. In some embodiments, the tablet or capsule comprises 15 to 25 mg terlipressin. In some embodiments, the tablet or capsule comprises 18 to 22 mg terlipressin. In some embodiments, the tablet or capsule comprises 20 mg terlipressin.

In some embodiments, the subject is administered 5 to 100 mg terlipressin daily (e.g., 20 to 100 mg terlipressin daily, 40 to 100 mg terlipressin daily, 60 to 100 mg terlipressin daily, e.g., 80 mg terlipressin).

In some embodiments, multiple tablets or capsules are administered 2 times daily. In some embodiments, multiple tablets or capsules are administered 3 times daily.

In some embodiments, the subject is administered at least 10, 20, 30, 40, 50, 60 mg terlipressin daily.

In some embodiments, the method results in reduced side effects relative to a method of administering terlipressin by other forms of administration (e.g., intravenous administration).

In some embodiments, the method provides greater patient compliance (e.g., compliance by a subject described herein) relative to a method of administering terlipressin by other forms of administration (e.g., intravenous administration).

In an aspect, provided is a method of treating a subject suffering from ascites (e.g. associated with to liver cirrhosis), the method comprising orally administering a pharmaceutical composition (e.g., solid dosage composition, oral dosage form) configured as a tablet or capsule comprising a therapeutically effective amount (e.g., at least 5 mg (e.g., 5, 7, 10, 15, 17, 20, 25, 30 mg)) of terlipressin or a pharmaceutically acceptable salt thereof, 1, 2, 3, or 4 times daily, thereby treating the subject.

In some embodiments, the tablet or capsule is administered 1 to 4 times daily. In some embodiments, the tablet or capsule is administered 1 or 2 times daily. In some embodiments the tablet or capsule is administered 2 times daily. In some embodiments the tablet or capsule is administered 4 times daily. In some embodiments the tablet or capsule is administered 3 times daily.

In some embodiments, the tablet or capsule comprises 5 to 30 mg terlipressin. In some embodiments, the tablet or capsule comprises 10 to 30 mg terlipressin. In some embodiments, the tablet or capsule comprises 15 to 25 mg terlipressin. In some embodiments, the tablet or capsule comprises 18 to 22 mg terlipressin. In some embodiments, the tablet or capsule comprises 20 mg terlipressin.

In some embodiments, the subject is administered 5 to 100 mg terlipressin daily (e.g., 20 to 100 mg terlipressin daily, 40 to 100 mg terlipressin daily, 60 to 100 mg terlipressin daily, e.g., 80 mg terlipressin).

In some embodiments, multiple tablets or capsules are administered 1 or 2 times daily. In some embodiments, multiple tablets or capsules are administered 3 times daily.

In some embodiments, the subject is administered at least 10, 20, 30, 40, 50, 60 mg terlipressin daily.

In some embodiments, the method results in reduced side effects relative to a method of administering terlipressin by other forms of administration (e.g., intravenous administration).

In some embodiments, the method provides greater patient compliance (e.g., compliance by a subject described herein) relative to a method of administering terlipressin by other forms of administration (e.g., intravenous administration).

In an aspect, provided is a unit dosage formulation for oral administration (an oral dosage form) which comprises a therapeutically effective amount of terlipressin, or a pharmaceutically acceptable salt thereof (e.g., at least 5 mg e.g., 5, 7, 10, 15, 17, 20, 25, 30 mg) of terlipressin, or a pharmaceutically acceptable salt thereof).

In some embodiments, the oral dosage formulation (i.e., oral dosage form) comprises about 5, 10, 15, 20, 25, 30, or 50 mg terlipressin.

In some embodiments, the oral dosage form comprises 5 to 50 mg (e.g., 5 to 40 mg, 5 to 30 mg, 5 to 25 mg, 15 to 25 mg, 18 to 22 mg) terlipressin. In some embodiments, the formulation comprises at least 5 mg terlipressin.

In some embodiments, the oral dosage form is enteric-coated.

In some embodiments, the oral dosage formulation (i.e., oral dosage form) described herein is used for treatment of a subject suffering from hypotension (e.g., neurogenic orthostatic hypotension or postprandial hypotension) or portal hypertension or ascites.

In an aspect, provided is an oral dosage formulation (i.e., oral dosage form) comprising a therapeutically effective amount of terlipressin, or a pharmaceutically acceptable salt thereof (e.g., at least 5 mg e.g., 5, 7, 10, 15, 17, 20, 25, 30 mg) of terlipressin, or a pharmaceutically acceptable salt thereof).

In some embodiments, the oral dosage formulation (i.e., oral dosage form) comprises about 5, 10, 15, 20, 25, 30, or 50 mg terlipressin. In some embodiments, the oral dosage formulation (i.e., oral dosage form) comprises 5 to 50 mg (e.g., 5 to 40 mg, 5 to 30 mg, 5 to 25 mg, 15 to 25 mg, 18 to 22 mg) terlipressin. In some embodiments, the dosage form comprises at least 5 mg terlipressin.

In some embodiments, the oral dosage formulation (i.e., oral dosage form) is additionally enteric-coated.

In an aspect, provided is a capsule containing the composition comprising a therapeutically effective amount of terlipressin, or a pharmaceutically acceptable salt thereof (e.g., at least 5 mg (e.g., 5, 7, 10, 15, 17, 20, 25, 30 mg)) of terlipressin, or a pharmaceutically acceptable salt thereof).

In some embodiments, the capsule is a hard gel or a soft gel capsule.

In some embodiments, the capsule comprises about 5, 10, 15, 20, 25, 30, or 50 mg terlipressin. In some embodiments, the capsule comprises 5 to 50 mg (e.g., 5 to 40 mg, 5 to 30 mg, 5 to 25 mg, 15 to 25 mg, 18 to 22 mg) terlipressin. In some embodiments, the capsule comprises at least 5 mg terlipressin. In some embodiments, the capsule is enteric-coated.

In an aspect, provided is a tablet comprising a therapeutically effective amount of terlipressin, or a pharmaceutically acceptable salt thereof (e.g., at least 5 mg (e.g., 5, 7, 10, 15, 17, 20, 25, 30 mg)) of terlipressin, or a pharmaceutically acceptable salt thereof).

In an aspect, provided is a kit comprising instructions and the dosage form descried herein.

In an aspect, provided is a method of treating a subject suffering from neurogenic orthostatic hypotension or postprandial hypotension, the method comprising administration to the subject of a therapeutically effective amount of an oral terlipressin in combination with a therapeutically effective amount of fludrocortisone.

In an aspect, provided is a method of treating a subject suffering from neurogenic orthostatic hypotension or postprandial hypotension, the method comprising administration to the subject of a therapeutically effective amount of an oral terlipressin in combination with a therapeutically effective amount of fludrocortisone and optionally in combination with a bolus of water. A bolus of water may be about 100, 200, 300, 400 or 500 ml of water or more.

In an aspect, provided is a unit dosage formulation for oral administration (oral dosage form) comprising a therapeutically effective amount of terlipressin in combination with a therapeutically effective amount of fludrocortisone.

In an aspect, provided is a method of treatment of a subject suffering from portal hypertension/bleeding esophageal varices, the method comprising administration to the subject of a therapeutically effective amount of an oral terlipressin in combination with a therapeutically effective amount of a liver fibrosis agent.

In an aspect, provided is a unit dosage formulation for oral administration (oral dosage form) comprising a therapeutically effective amount of terlipressin in combination with a therapeutically effective amount of a liver fibrosis agent.

In an aspect, provided is a method of treatment of a subject suffering from ascites, the method comprising administration to the subject of a therapeutically effective amount of an oral terlipressin in combination with a therapeutically effective amount of a diuretic.

In an aspect, provided is a unit dosage formulation for oral administration (oral dosage form) comprising a therapeutically effective amount of terlipressin in combination with a therapeutically effective amount of a diuretic.

In an aspect, provided is a method of treatment of a subject suffering from ascites, the method comprising administration to the subject of a therapeutically effective amount of an oral terlipressin in combination with a therapeutically effective amount of albumin.

In an aspect, provided is a method of treatment of a subject suffering from ascites, the method comprising administration to the subject of a therapeutically effective amount of an oral terlipressin in combination with a therapeutically effective amount of a beta-blocker.

In an aspect, provided is a unit dosage formulation for oral administration (oral dosage form) comprising a therapeutically effective amount of terlipressin in combination with a therapeutically effective amount of a beta-blocker.

In some aspects, a composition described herein improves the absorption in the gastrointestinal (GI) tract of terlipressin, wherein terlipressin is otherwise in a composition or dosage form that is generally characterized by low or zero oral bioavailability and/or absorption, e.g., low or zero bioavailability, e.g., in aqueous solution, and in other oral formulations known in the art. In at least one aspect, a composition described herein improves bioavailability by enhancing the GI wall/barrier permeability to terlipressin. For example, a composition described herein may facilitate absorption by permeating the GI wall/barrier primarily via unsealing of the tight junctions between GI epithelial cells, although it may also work by transcellular absorption. In some embodiments, the BA of terlipressin is at least 0.5%, at least 1%, at least 2%, or at least 3% or more.

Described herein is a process for producing a pharmaceutical composition (bulk drug product) which involves preparing a water soluble composition comprising a therapeutically effective amount of terlipressin and a medium chain fatty acid salt (and other ingredients—see below), drying (e.g., by lyophilization) the water soluble composition to obtain a solid powder, and suspending the lyophilized material (the solid powder) in a hydrophobic (oily) medium, preferably castor oil or glyceryl tricaprylate (including other ingredients, e.g. a PVP polymer and surfactants and viscosity modifiers—see below), to produce a suspension containing in solid form terlipressin and the medium chain fatty acid salt, thereby producing the bulk drug product, which contains at least 10% by weight of medium chain fatty acid salt (e.g., at least 11%, at least 12%, or greater). The solid form may comprise a particle (e.g., consists essentially of particles, or consists of particles). The particle may be produced by lyophilization, by spray drying or by granulation. The bulk drug product may then be encapsulated in capsules which can be coated by a pH sensitive coating (e.g., an enteric coating) and may be used for oral delivery.

Thus, in one aspect the invention features a composition. The composition includes terlipressin and a medium chain fatty acid salt associated with a substantially hydrophobic medium, e.g., castor oil, wherein terlipressin and the medium chain fatty acid salt are in solid form, e.g. in the same solid form such as a particle, obtained by drying from an aqueous medium, e.g. by lyophilizing the aqueous medium, and wherein the medium chain fatty acid salt is present at 10% by weight or more, preferably 12-15%, e.g., about 12%, about 13%, about 14%, or about 15% or about 16%, or about 17%. In some embodiments, the composition contains other ingredients (as described herein).

The present compositions of the invention are not emulsions. In embodiments, the compositions are oily suspensions and the amount of water in the compositions is very low (e.g., less than 1%, less than 0.5%, less than 0.1%).

In the compositions of the invention, terlipressin and the medium chain fatty acid salt are in intimate contact with the substantially hydrophobic medium. For example, a powder comprising terlipressin and medium chain fatty acid salt is coated, immersed or suspended in the substantially hydrophobic medium.

During the production process, the aqueous medium which contains terlipressin and the medium chain fatty acid salt and the other ingredients is dried (e.g. by lyophilization) to obtain the hydrophilic fraction which is a powder (e.g., a solid form comprising a plurality of particles), and a particle in that powder contains all the ingredients i.e. terlipressin and medium chain fatty acid salt are together in a single particle. The solid form may be, for example, a granulated particle or a lyophilized particle.

In some embodiments, the composition includes a plurality of medium chain fatty acid salts and derivatives thereof. For example, the solid particle may further include a plurality of medium chain fatty acid salts and derivatives thereof.

In some embodiments, the medium chain fatty acid salt is selected from the group consisting of sodium hexanoate, sodium heptanoate, sodium octanoate, sodium nonanoate, sodium decanoate, sodium undecanoate, sodium dodecanoate, sodium tridecanoate, and sodium tetradecanoate or a combination thereof. In accordance with one or more embodiments, the composition is substantially free of sodium dodecanoate, sodium tridecanoate, and sodium tetradecanoate. In some embodiments, the medium chain fatty acid is sodium octanoate and the sodium octanoate is present at a concentration of above 10% e.g. about 11% to about 50% weight/weight (wt/wt). In other embodiments, the medium chain fatty acid is sodium decanoate. In some embodiments, the sodium decanoate is present at a concentration of above 10%, e.g., about 11% to about 50% weight/weight (wt/wt).

In some embodiments, the substantially hydrophobic medium comprises a triglyceride. For example, the triglyceride may be selected from the group consisting of glyceryl tributyrate, glyceryl monooleate, glyceryl monocaprylate and glyceryl tricaprylate.

In some embodiments, the substantially hydrophobic medium comprises mineral oil, castor oil, olive oil, corn oil, coconut oil, peanut oil, soybean oil, cotton seed oil, sesame oil or canola oil, or combinations thereof.

In some embodiments, the water-soluble composition contains a medium chain fatty acid salt and the hydrophobic medium contains the corresponding medium chain fatty acid; in some particular embodiments, the medium chain fatty acid salt is a salt of octanoic acid such as sodium octanoate and the medium chain fatty acid is octanoic acid.

In some embodiments, the water-soluble composition contains a medium chain fatty acid salt and the hydrophobic medium contains the corresponding medium chain monoglyceride or the corresponding medium chain triglyceride or a combination thereof; in some particular embodiments, the medium chain fatty acid salt is sodium octanoate and the monoglyceride is glyceryl monocaprylate and the triglyceride is glyceryl tricaprylate.

In some embodiments, the composition further includes one or more excipients. The excipients may be a salt e.g. $MgCl_2$ or an amine containing compound or mannitol. In some embodiments, the excipient is in the same solid form as terlipressin.

In some embodiments, the composition further includes one or more surfactants. For example, the surfactant may be selected from the group consisting of sorbitan monopalmitate (Span-40®), polyoxyethylene sorbitan monooleate (Tween80), lecithin, and glyceryl monooleate (GMO). In one or more embodiments, the surfactant comprises from about 0.1% to about 6% by weight of the composition.

In preferred embodiments, the composition is an oral dosage form. For example, the composition may be filled in a hard or soft capsule.

The pharmaceutical compositions described herein include incorporation of terlipressin as a therapeutic agent within an oral dosage form which is enteric-coated. An oral dosage form according to the invention comprises additives or excipients that are suitable for the preparation of the oral dosage form according to the present invention. The oral dosage form may comprise tablets or capsules, preferably enteric coated.

In some embodiments, the bioavailability of terlipressin, when administered to a subject, is at least 0.5%-2% relative to parenteral (subcutaneous or intravenous) administration. In some embodiments, the composition, when administered to a subject, provides above 0.5%, above 1%, above 2%, above 3%, above 5%, above 10%, or above 20% or above 30% absorption of terlipressin across a biological barrier. The levels of absorption achieved produce the therapeutic levels needed for the indication concerned.

The formulations of the invention allow incorporation of terlipressin into the formulation without any chemical modification or degradation of terlipressin. Furthermore, the formulations of the invention allow for high flexibility in loading of terlipressin. Finally, the formulations of the invention protect the cargo compounds from inactivation in the GI environment due to for example proteolytic degradation and oxidation.

In some embodiments, the method may include encapsulating the suspension to form a capsule. The method may further include coating the capsule, e.g., with an enteric coating.

In some embodiments, the method may include providing instructions to administer the capsule to a subject. The instructions may relate to administering the capsule to a subject for any indication described herein. In one aspect, the invention features capsules provided with instructions relating to administering the capsule to a subject for any indication described herein.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments.

The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

Throughout this application, various publications, including United States patents, are referenced by author and year and patents and applications by number. The disclosures of these publications and patents and patent applications in their entireties are hereby incorporated by reference into this application in order to more fully describe the state of the art to which this invention pertains.

BRIEF DESCRIPTION OF THE DRAWINGS

Various aspects of at least one embodiment are discussed below with reference to the accompanying Figures. The Figures are provided for the purposes of illustration and explanation and are not intended as a definition of the limits of the invention. In the Figures:

FIG. 1A. Pharmacokinetics for terlipressin administered intravenously to dogs at dosage of 0.2 mg.

FIG. 1B. Pharmacokinetics for terlipressin administered orally by means of capsules to dogs at dosage of 20 mg.

DETAILED DESCRIPTION

Provided herein are methods of treating a subject suffering from hypotension (e.g., neurogenic orthostatic hypotension or postprandial hypotension) portal hypertension (e.g., bleeding esophageal varices associated with portal hypertension) or ascites, the method comprising administering a therapeutically effective amount (e.g., at least 5 mg (e.g., 5, 7, 10, 15, 17, 20, 25, 30 mg)) of terlipressin 1, 2, 3, or 4 times daily, thereby treating the subject.

Hypotension:

Neurogenic Orthostatic Hypotension

Neurogenic Orthostatic Hypotension (nOH) is a subtype of orthostatic hypotension that occurs in people with an existing neurologic disease (e.g., neurological conditions that are chronic and irreversible). In some embodiments, the neurologic disease is Parkinson's Disease or Multi-System Atrophy (MSA) or pure autonomic failure. Orthostatic (postural) hypotension refers to a reduction in systolic blood pressure (e.g., of at least 20 mm Hg) or a reduction in diastolic blood pressure (e.g., of at least 10 mm Hg) during the first 3 minutes of standing. Neurogenic orthostatic hypotension can be caused by autonomic nervous system malfunction, which is the part of the nervous system controlling involuntary body activity (e.g., keeping blood pressure normal). Symptoms include dizziness, lightheadedness, syncope (fainting), fatigue, blurry vision, weakness, trouble concentrating, head and neck pain. Outcomes include injuries such as tooth damage, broken bones, even death as a result of falling. Current pharmacologic treatments include fludrocortisone and/or midodrine, and/or pyridostigmine and/or droxidopa and/or erythropoietin; Lanier et al (2011) American Family Physician, 84(5), 527-536; and Editorial (1998) J. Neurol. Neurosurg Psychiatry 65:285-289. Drugs in development include Northera—norepinephrine pro-drug—(2014—Lundbeck/Chelsea) and TD-9855—norepinephrine and serotonin reuptake inhibitor—(P1/2—Theravance).

Intravenous injection of terlipressin has been shown to be effective in nOH (Rittig et al. (1991) Movement Disorders 6(1), p 21-28) at a level of 5-10 µg per kilogram of body weight; however, this method of administration is clearly not suitable for use as home therapy. The oral terlipressin dosage form of the invention can be administered as home therapy, and can be used, inter alia for the prophylaxis and treatment of orthostatic hypotension.

Postprandial Hypotension

Postprandial hypotension is commonly defined as a decrease in systolic blood pressure of 20 mmHg or more observed within two hours after meal ingestion. It is very common in older patients especially in those living in long-term healthcare homes. Patients with postprandial hypotension may develop symptomatic hypotension, syncope (fainting) and falls. See Lisk, R. (April 2010) *Postprandial hypotension* in www.gerimed.co.uk, Cardiology 203-206; Lubart et al (September 2006) Journal of the American Geriatrics Society, Vol. 54, Issue 9, pages 1377-1381, *Postprandial Hypotension in Long-Term Care Elderly Patients on Enteral Feeding*; and Trahair et el (2014) JAMDA 15, 394-409, *Postprandial Hypotension: A Systematic Review*. Hormonal treatments with intravenous vasopressin (see Hakusui et al (1991) Neurology 41(5), 712-715 are known to be effective, but they are unsuitable for home use.

The oral terlipressin dosage form of the invention can be administered as home therapy, and can be used, inter alia for the prophylaxis and treatment of postprandial hypotension.

Portal Hypertension/Bleeding Esophageal Varices

Portal hypertension, or bleeding esophageal varices (or other varices) associated with portal hypertension, can occur when blood flow to the liver is blocked (e.g., by severe liver scarring (cirrhosis) in the liver tissue resulting from liver disease); as a result, veins (varices), most commonly in the lower esophagus, rupture and bleed. Thus esophageal varices are a direct result of high blood pressure in the portal vein. Symptoms include vomiting and significant visible amounts of blood in vomit; stomach pain; black, tarry or bloody stools; lightheadedness; loss of consciousness; signs of liver disease (e.g., yellow coloration of the skin and eyes; easy bleeding or bruising; fluid buildup in the abdomen). Although esophageal varices are the most common varices produced as a result of portal hypertension, varices can also be produced in the stomach, rectum, or umbilical area.

In patients who survive the first episode of esophageal variceal hemorrhage, the risk of recurrent bleeding is as high as 60% with a mortality rate of up to 33%. Terlipressin is effective in control of variceal bleeding but is currently administered intravenously and therefore is not convenient for prophylaxis; see Biecker (2013) Hindawi Publishing Corp, ISRN Hepatology (2013), Article ID 541836 (20 pp). In some embodiments, the subject suffers from cirrhosis (i.e., the subject has severe scarring of the liver as a result, e.g., due to excessive alcohol consumption or serious infections, such as hepatitis). In some embodiments, the subject suffers from portal vein thrombosis (i.e., blood clotting inside the portal vein). In some embodiments, the subject suffers from hepatorenal syndrome and/or ascites which are frequent complication of liver cirrhosis. In some embodiments, the subject suffers from nonalcoholic fatty liver disease and/or nonalcoholic steatohepatitis (NASH) and/or primary biliary cirrhosis or a parasitic infection, schistosomiasis, which can damage the liver.

Intravenously administered vasoconstrictors such as terlipressin are used to treat acute variceal bleeding but there is a 60% re-bleed rate and 20% mortality. There are no approved therapies to prevent (or delay) re-bleeds of varices. There is off-label use of beta blockers. It is estimated that in the US there are 40 K secondary prophylaxis patients ineligible for beta blockers. Off-label beta-blockers are also the only long-term medication for prevention (or delay) of variceal bleeds.

Beta-adrenergic blocking agents are a class of medicines that bind to beta-adrenoreceptors and prevent the binding of norepinephrine and epinephrine at these receptors. This prevents sympathetic stimulation of the heart and reduces heart rate, cardiac contractility, conduction velocity, and relaxation rate which decreases myocardial oxygen demand and increases exercise tolerance. Beta-adrenergic blocking agents are commonly referred to as beta-blockers.

Beta-blockers can be grouped into those that are non-selective (block both beta-1 and beta-2 receptors, such as nadolol, penbutolol, pindolol, propranolol, sotalol, and timolol), and those that are cardioselective (only block beta-1 receptors, and include acebutolol, betaxolol, bisoprolol, esmolol, and metoprolol). Some, like atenolol, are only cardioselective at low dosages. Beta-blockers for treatment of variceal bleeding are normally non-selective beta blockers.

Currently there is no approved therapy for nonalcoholic fatty liver disease/nonalcoholic steatohepatitis (NASH); see Filozof (2015) 75:1373-1392 and Cassidy et al (2016 Nature reviews) 15, 745-746. See also Nusrat et al (2014) World J Gastroenterol 20(18) 5442-5460 and de Vries et al (2017) 37(1),123-129.

The oral terlipressin therapy of the present invention is suitable as an in-home therapy and can be used for prophylaxis and long-term management of varices (e.g., esophageal varices) and variceal bleeding.

Ascites

Ascites is a frequent and life-threatening complication of diseases such as advanced liver cirrhosis, heart failure, and cancer (malignant ascites), with an expected 40% mortality rate within two years of diagnosis. To date the US FDA has not approved any therapies specifically to treat ascites, although a few drugs (e.g., diuretics) are being used off-label with limited and temporary efficacy. First-line diuretic therapy for cirrhotic ascites is the use of spironolactone (Aldactone) preferably the combined use of spironolactone and furosemide (Lasix). Studies have shown the efficacy of terlipressin administered as intravenous (IV) bolus injections every 4 hours or administered as an intravenous infusion in patients with type 1 hepatorenal syndrome (HRS), alone and/or in combination with albumin; Angeli (2011) in Gerbes (ed) Ascites, Hyponatremia and Hepatorenal Syndrome: Progress in treatment Front Gastrointest Res. Basel, Karger vol 28, 187-189; Annamalai et al (2016) World J Hepatol 2016 Oct. 8; 8(28): 1182-1193; ISSN 1948-5182.

HRS is the beginning of renal failure and frequently occurs in patients with ascites that has become refractory to treatment with diuretics; Krag Hepatology—46(6) 1863-1871 DOI: 10.1002/hep.21901. Note that two forms of hepatorenal syndrome have been defined: Type 1 HRS entails a rapidly progressive decline in kidney function, while type 2 HRS is associated with ascites (fluid accumulation in the abdomen) that does not improve with standard diuretic medications. Refractory ascites is ascites that cannot be mobilized or for which early recurrence after therapeutic paracentesis cannot be satisfactorily prevented by medical therapy. This includes two different subgroups:

Diuretic resistant ascites—ascites that is refractory to dietary sodium restriction and intensive diuretic treatment (spironolactone 400 mg/day and furosemide 160 mg/day for at least one week, and a salt restricted diet of less than 90 mmol/day (5.2 g of salt)/day).

Diuretic intractable ascites—ascites that is refractory to therapy due to the development of diuretic induced complications that preclude the use of an effective diuretic dosage.

Refractory ascites is sometimes treated by aquaretics (e.g., vasopressin V2-receptor antagonists also known as vaptans, e.g., lixivaptan, satavaptan, tolvaptan) which promote excretion of electrolyte-free water and thus might be beneficial in patients with ascites and hyponatremia. See Habib and Boyer (2012) Ther Adv Gastroenterol, 5(3) 189-197. Intravenous treatment of terlipressin, optionally in combination with diuretics, may resolve refractory ascites in hospitalized patients.

However, these intermittent high-dose IV injections (typically 1 or 2 mg in a single dose) carry a high risk of side-effects. More recent studies with hospitalized HRS patients indicate that a continuous infusion of terlipressin can achieve similar efficacy to intermittent injections with a much better safety profile. Recently there have been reports of treating ascites by administering terlipressin by continuous infusion in non-hospitalized patients (see U.S. Pat. No. 9,655,945 of Angeli et al). However, this is still an invasive procedure with the attendant risks (such as infection) and inconvenience involved. Additionally, these patients are at risk of systemic hypotension, and intravenous dosing of terlipressin may heighten this risk because of its short Tmax. The oral terlipressin therapy for ascites described herein is suitable for out-patient administration and can be better tolerated in terms of hypotension risk due to a longer terlipressin Tmax.

Methods of Treatment

One embodiment of the invention relates to a method of treating a subject suffering from a disease or disorder which comprises orally administering to the subject a therapeutically effective amount of terlipressin; the disease or disorder may be, for example, orthostatic hypotension, portal hypertension, bleeding varices (e.g. esophageal varices) and ascites (e.g., ascites associated with liver cirrhosis) and associated symptoms and side-effects thereof. Another embodiment of the invention relates to a composition of terlipressin for use in treating orally a disease or disorder in a subject.

Another embodiment of the invention relates to the use of terlipressin in the manufacture of a medicament by the process of the invention for the treatment of a disorder.

In some embodiments, the methods described herein treat a subject suffering from hypotension (e.g., neurogenic orthostatic hypotension), the method comprising administering one or two doses (e.g., a dose comprising 1 to 2 (or more) tablets or capsules comprising terlipressin) 15, 20, 30, 40, 45, or 60 minutes before getting up (e.g., in the morning or afternoon; before 4 or 5 pm), for example daily. In some embodiments, the tablet or capsule comprising terlipressin is about 2 to about 30 mg (e.g., about 5 to about 30 mg, about 10 to about 30 mg, about 15 to about 25 mg, about 18 to about 22 mg, about 20 mg, about 22 mg) terlipressin.

In some embodiments, the methods described herein treat a subject suffering from hypotension (e.g., postprandial hypotension) the method comprising administering one or two doses (e.g., a dose comprising 1 to 2 (or more) tablets or capsules comprising terlipressin).

In some embodiments, the methods described herein treat a subject suffering from portal hypertension or bleeding esophageal varices associated with portal hypertension, the method comprising administering oral terlipressin in a therapeutically effective amount.

In one aspect 1 to 4 doses (e.g., a dose comprising 1 to 2 tablets or capsules comprising terlipressin) are administered daily. In some embodiments, the tablet or capsule comprising terlipressin is about 2 to about 30 mg (e.g., about 5 to about 30 mg, about 10 to about 30 mg, about 15 to about 25 mg, about 18 to about 22 mg, about 20 mg, about 22 mg) terlipressin. In some embodiments, the terlipressin is administered orally for prevention of recurrence after a treated episode of bleeding varices. In some embodiments, the subject is able to return home while maintaining treatment (which is not possible with current intravenous administration of terlipressin). In some embodiments, oral terlipressin formulations may be used for primary and secondary prophylaxis of variceal bleeding.

In some embodiments, the methods described herein treat a subject suffering from portal hypertension or bleeding esophageal varices associated with portal hypertension, the method comprising administering 1 to 4 doses (e.g., a dose comprising 1 to 2 tablets or capsules comprising terlipressin) daily. In some embodiments, the tablet or capsule comprising terlipressin contains about 2 to about 30 mg (e.g., about 5 to about 30 mg, about 10 to about 30 mg, about 15 to about 25 mg, about 18 to about 22 mg, about 20 mg, about 22 mg) terlipressin.

In some embodiments, the methods described herein relate to administration of compositions described herein, e.g., a composition comprising terlipressin, for the treatment of hypotension, e.g., neurogenic orthostatic hypotension or postprandial hypotension; or hypertension, e.g., portal hypertension (e.g., bleeding esophageal varices associated with portal hypertension); or ascites (e.g., associated with liver cirrhosis). In some embodiments, the methods described herein comprise administration of a composition comprising terlipressin in an oral dosage form (e.g., comprising 1, 2, 3, 4, 5, 7, 10, 15, 17, 20, 25, 30, 40, 50 mg terlipressin).

Another aspect of this invention is a method for treating a subject suffering from neurogenic orthostatic hypotension, the method comprising administration to the subject of a therapeutically effective amount of terlipressin in combination with another drug used for treatment of neurogenic orthostatic hypotension. For example, the drugs to be used in combination with oral terlipressin include mineralocorticoids including but not limited to fludrocortisone and/or midodrine, and/or pyridostigmine and/or droxidopa and/or erythropoietin and/or Northera and/or TD-9855.

Another aspect of this invention is a method for treating a subject suffering from postprandial hypotension, the method comprising administration to the subject of a therapeutically effective amount of terlipressin in combination with another drug used for treatment of postprandial hypotension. For example, compounds to be used in combination with oral terlipressin include one or more of acarbose and guar gum and midodrine and/or Northera and/or TD-9855.

In some embodiments, oral terlipressin is administered in combination with a large volume (a bolus) of physiological liquid (e.g., 100 mL, 200 mL, 500 mL or greater volume of physiological liquid).

Another aspect of this invention is a unit dosage formulation for oral administration (oral dosage form) comprising terlipressin and a second or third oral drug used in treatment of neurogenic orthostatic hypotension, including mineralocorticoids including but not limited to fludrocortisone and/or midodrine, and/or pyridostigmine and/or droxidopa and/or erythropoietin and/or Northera and/or TD-9855.

Another aspect of this invention is a unit dosage formulation for oral administration (oral dosage form) comprising terlipressin and a second or third oral drug used in treatment of postprandial hypotension, including but not limited to acarbose, guar gum and midodrine and/or Northera and/or TD-9855.

Another aspect of this invention is a unit dosage formulation for oral administration (oral dosage form) comprising a therapeutically effective amount of terlipressin in combination with a therapeutically effective amount of fludrocortisone.

In some embodiments, oral terlipressin is administered in combination with a large volume of physiological liquid (e.g., 100 mL, 200 mL, 500 mL or greater volume of physiological liquid).

Another aspect of this invention is a method for treating a subject suffering from portal hypertension/bleeding esophageal varices, the method comprising administration to the subject of a therapeutically effective amount of terlipressin in combination with another drug used for treatment of portal hypertension/bleeding esophageal varices. Such drugs to be used in combination with oral terlipressin include beta blockers and isosorbide mononitrate. Non-drug therapies that may be used in combination with oral terlipressin include but are not limited to endoscopic ligation, sclerotherapy and surgical shunts.

Another aspect of this invention is a method for treating a subject suffering from cirrhosis, portal hypertension/bleeding esophageal varices, the method comprising administration to the subject of a therapeutically effective amount of terlipressin in combination with another drug used for treatment of hepatitis C. Such drugs to be used in combination with oral terlipressin include alfa-interferon such as Peg-IFN-2a or IFN-a-2b.

Another aspect of this invention is a method for treating a subject suffering from cirrhosis, portal hypertension/bleeding esophageal varices, the method comprising administration to the subject of a therapeutically effective amount of terlipressin in combination with another drug used for treatment of hepatitis B. Such drugs to be used in combination with oral terlipressin include Lamivudine, Telbivudine, Entecavir, Adefovir, and Tenofovir.

Another aspect of this invention is a method for treating a subject suffering from cirrhosis, portal hypertension/bleeding esophageal varices, the method comprising administration to the subject of a therapeutically effective amount of terlipressin in combination with another drug used for treatment of fibrosis and/or nonalcoholic steatohepatitis (NASH) and/or primary biliary cirrhosis. Such drugs to be used in combination with oral terlipressin include pirfenidone, nintedanib, obeticholic acid, urodeoxycholic acid and emricasan all administered orally; also vitamin E and pioglitazone.

Another aspect of this invention is a unit dosage formulation for oral administration (oral dosage form) comprising a therapeutically effective amount of terlipressin in combination with a therapeutically effective amount of a liver fibrosis agent.

One embodiment of the invention relates to a method for treating a subject suffering from ascites associated with liver cirrhosis, the method comprising orally administering a therapeutically effective amount of terlipressin or a pharmaceutically acceptable salt thereof thereby treating the subject. In one aspect 1 to 4 doses (e.g., a dose comprising 1 to 2 or more tablets or capsules comprising terlipressin) are administered daily. In some embodiments, the tablet or capsule comprising terlipressin contains about 2 to about 30 mg (e.g., about 5 to about 30 mg, about 10 to about 30 mg, about 15 to about 25 mg, about 18 to about 22 mg, about 20 mg, about 22 mg) terlipressin. In some embodiments of the method of the invention, the subject is administered 5 to 100 mg terlipressin daily (e.g., 20 to 100 mg terlipressin daily, 40 to 100 mg terlipressin daily, 60 to 100 mg terlipressin daily, e.g., 80 mg terlipressin daily). In some embodiments the terlipressin is administered for about one day to about 12 months. In some embodiments the condition of the subject has not progressed to hepatorenal syndrome (HRS). In some embodiments the administration of terlipressin is provided on an out-patient basis. In some embodiments the terlipressin dose escalates over the about one day to about 12 months. One aspect of the invention is a method for reducing the volume of ascitic fluid prior to, during or following a paracentesis procedure in a subject suffering from ascites, the method comprising orally administering a therapeutically effective amount of terlipressin or a pharmaceutically acceptable salt thereof. In one aspect 1 to 4 doses (e.g., a dose comprising 1 to 2 or more tablets or capsules comprising terlipressin) are administered daily. In some embodiments, the tablet or capsule comprising terlipressin contains about 2 to about 30 mg (e.g., about 5 to about 30 mg, about 10 to about 30 mg, about 15 to about 25 mg, about 18 to about 22 mg, about 20 mg, about 22 mg) terlipressin. In one embodiment the subject is administered 5 to 200 mg terlipressin daily (e.g., 20 to 100 mg terlipressin daily, 40 to 100 mg terlipressin daily, 60 to 100 mg terlipressin daily, e.g., 80 mg terlipressin daily). In another embodiment the terlipressin is administered for about one day to about 12 months. In another embodiment the condition of the subject has not progressed to hepatorenal syndrome (HRS). In another embodiment the administration is provided on an out-patient basis.

Another embodiment of the invention is a method for improving renal function in a subject suffering from ascites, the method comprising orally administering a therapeutically effective amount of terlipressin or a pharmaceutically acceptable salt thereof. In one aspect the improvement comprises a reduction in serum creatinine concentration and/or an increase in plasma sodium concentration and/or an increase in urinary sodium excretion and/or a decrease in urea concentration in serum. In one aspect 1 to 4 doses (e.g., a dose comprising 1 to 2 or more tablets or capsules comprising terlipressin) are administered daily. In some embodiments, the tablet or capsule comprising terlipressin is about 2 to about 30 mg (e.g., about 5 to about 30 mg, about 10 to about 30 mg, about 15 to about 25 mg, about 18 to about 22 mg, about 22 mg) terlipressin. In one aspect the subject is administered 5 to 200 mg terlipressin daily (e.g., 20 to 100 mg terlipressin daily, 40 to 100 mg terlipressin daily, 60 to 100 mg terlipressin daily, e.g., 80 mg terlipressin daily). In another aspect the terlipressin is administered for about one day to about 12 months. In another aspect the condition of the subject has not progressed to hepatorenal syndrome (HRS). In another aspect the administration is provided on an out-patient basis. In another aspect the terlipressin dose escalates over the about one day to about 12 months. Another embodiment of the invention is a method for correcting hyponatremia in a subject suffering from ascites, the method comprising orally administering to the subject a therapeutically effective amount of terlipressin or a pharmaceutically acceptable salt thereof. In one aspect 1 to 4 doses (e.g., a dose comprising 1 to 2 or more tablets or capsules comprising terlipressin) are administered daily. In some embodiments, the tablet or capsule comprising terlipressin is about 2 to about 30 mg (e.g., about 5 to about 30 mg, about 10 to about 30 mg, about 15 to about 25 mg, about 18 to about 22 mg, about 20 mg, about 22 mg) terlipressin. In one aspect the subject is administered 5 to 200 mg terlipressin daily (e.g., 20 to 100 mg terlipressin daily, 40 to 100 mg terlipressin daily, 60 to 100 mg terlipressin daily, e.g., 80 mg terlipressin daily). In another aspect, the terlipressin is administered for about one day to about 12 months. In one aspect the condition of the subject has not progressed to hepatorenal syndrome (HRS). In another aspect the administration is provided on an out-patient basis.

Another aspect of the invention relates to a method for treating a subject suffering from a disease or disorder (such as cirrhosis, portal hypertension, and bleeding varices, ascites, including symptoms and side-effects thereof) which comprises orally administering to the subject a therapeutically effective amount of terlipressin in combination with a diuretic and/or in combination with albumin and/or in combination with a beta blocker.

One embodiment of the invention relates to a unit dosage formulation for oral administration (oral dosage form) comprising a therapeutically effective amount of terlipressin in combination with a therapeutically effective amount of at least one diuretic and/or at least one a beta-blocker. One aspect of that embodiment is a unit dosage formulation (oral dosage form) for treatment of a subject suffering from ascites.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

In some embodiments, the methods described herein treat a subject suffering from hypotension (e.g., neurogenic orthostatic hypotension or postprandial hypotension), the method comprising administering one or two doses (e.g., a dose comprising 1 to 2 or more tablets or capsules comprising terlipressin) 15, 20, 30, 40, 45, or 60 minutes before getting up (e.g., in the morning or afternoon; before 4 or 5 pm), for example daily. In some embodiments, the tablet or capsule comprising terlipressin is about 10 to about 30 mg (e.g., about 15 to about 25 mg, about 18 to about 22 mg, about 22 mg) terlipressin.

Subjects

Described herein are methods for treating hypotension (e.g., neurogenic orthostatic hypotension or postprandial hypotension) portal hypertension (e.g., bleeding esophageal varices associated with portal hypertension) or ascites in a subject. In some embodiments, the subject suffers from a neurological condition. In some embodiments, the neurological condition is chronic or irreversible (e.g., the condition is chronic and irreversible). In some embodiments, the subject suffers from Parkinson Disease or Multi-System Atrophy (MSA). In some embodiments, the subject suffers from Non-Alcoholic Fatty Liver Disease (NAFLD) or Non-Alcoholic Steatohepatitis (NASH). In some embodiments, the subject suffers from Hepatorenal Syndrome (HRS) (e.g., HRS type 1 or HRS type 2). In some embodiments the subject suffers from cancer. In some embodiments the subject suffers from heart failure.

Dosing and Administration

Described herein are methods for treating hypotension (e.g., neurogenic orthostatic hypotension or postprandial hypotension), portal hypertension (e.g., bleeding esophageal varices associated with portal hypertension) or ascites in a subject, the method comprising administration of a composition comprising terlipressin. In some embodiments, the methods described herein comprise oral administration of a composition comprising terlipressin. In some embodiments, the methods described herein comprise administration of a composition comprising terlipressin in an oral dosage form (e.g., comprising 1, 2, 3, 4, 5, 7, 10, 15, 17, 20, 25, 30, 40, 50 mg terlipressin).

In some embodiments, the methods described herein provide about 1 to about 1000 μg/mL terlipressin concentration in a subject. In some embodiments, the methods described herein provide about 10 to about 600 μg/mL terlipressin concentration in a subject, e.g., in the plasma of the subject. In some embodiments, the methods described herein provide about 20 to about 200 μg/mL terlipressin concentration in a subject. In some embodiments, the methods described herein provide about 60 μg/mL terlipressin concentration in a subject.

In some embodiments, the methods described herein provide about 1 to about 200 μg/mL (lysine-) vasopressin concentration in a subject. (Vasopressin is the active metabolite of terlipressin.) In some embodiments, the methods described herein provide about 2 to about 100 μg/mL vasopressin concentration in a subject, e.g., in the plasma of the subject. In some embodiments, the methods described herein provide about 3 to about 30 μg/mL vasopressin concentration in a subject. In some embodiments, the methods described herein provide about 10 μg/mL vasopressin concentration in a subject In some embodiments, the composition is configured in a solid dosage form. In some embodiments, the solid dosage form is a capsule, e.g., with an enteric coating. In some embodiments, the solid dosage form is a tablet e.g., with an enteric coating.

In some embodiments, the capsule contains 5, 10, 15, 20, 25, 30, 50 mg terlipressin. In some embodiments, the capsule contains about 15 to about 25 mg terlipressin. In some embodiments, the capsule contains about 18 to about 22 mg terlipressin. In some embodiments, the capsule contains 20 mg terlipressin.

In some embodiments, the tablet contains 5, 10, 15, 20, 25, 30, 50 or 100 mg terlipressin.

In some embodiments, the method comprises administration up to 2 times per day.

In some embodiments, the method comprises administration up to 3 or 4 times per day.

The dosage regimen utilizing the compounds is selected in accordance with a variety of factors including age, weight, sex and medical condition of the patient; the severity of the condition to be treated; the route of administration; the renal and hepatic function of the patient; and the particular compound or salt thereof employed. An ordinarily skilled physician can readily determine and prescribe the effective amount of the drug required to prevent, counter or arrest the progress of the condition. Oral dosages of the present invention, when used for the indicated effects, may be provided in the form of capsules comprising 0.3, 0.5, 1, 1.5, 2, 4, 5, 10, 15, 17, 19, 20, 21, 23, 25, 30, 35, 40, 45, 50 mg or more of therapeutic agent (e.g., terlipressin). In some embodiments, the oral dosage comprising the therapeutic agent (e.g., terlipressin) is a 1, 1.5, 2, 4, 5, 10, 15, 17, 19, 20, 21, 23, 25, 30, 35, 40, 45, 50 mg or more solid dosage form (e.g., capsule (e.g., capsule with an enteric coating), tablet). In some embodiments, the capsule is a 5, 10, 15, 20, 25, 30, 50 or 100 mg capsule. In some embodiments, the capsule is about 15 to about 25 mg. In some embodiments, the capsule is about 18 to about 22 mg. In some embodiments, the capsule is a 20 mg capsule.

In some embodiments, the oral dosage comprises about 0.3 to about 50 mg of terlipressin (e.g., about 1 to about 50 mg of terlipressin, about 5 to about 50 mg of terlipressin, about 10 to about 40 mg of terlipressin, about 10 to about 30 mg of terlipressin, about 15 to about 25 mg of terlipressin, about 18 to about 22 mg of terlipressin, about 20 mg terlipressin).

In some embodiments, the oral dosage comprises at least 0.1, 0.3, 0.5, 1, 1.5, 2, 4, 5, 10, 15, 17, 19, or 20 mg terlipressin.

Compositions described herein may be administered in a single daily dose, or the total daily dosage may be administered in divided doses of two, three or four times daily. In some embodiments, the method comprises administration up to 2 times per day. In some embodiments, the composition is administered up to 3 or 4 times per day.

In some embodiments, the composition is administered at a daily dose of from about 1 to about 200 mg/day (e.g., about 1 to about 100 mg/day, about 5 to about 100 mg/day, about 5 to about 50 mg/day), e.g., administered at least 1, 2, 3, or 4 times daily (e.g., in the morning, in the afternoon). In some embodiments, the composition is administered once or twice a day. In some embodiments for treating hypotension (e.g., neurogenic orthostatic hypotension), the composition is administered 15, 20, 30, 45, or 60 minutes prior to getting up (e.g., getting up in the morning, getting up after a nap e.g. an afternoon nap). In some embodiments, the composition is not administered in the late afternoon or evening (e.g., the composition is not administered after 4 or 5 pm); without being bound by theory, to prevent supine hypertension. For example, the composition comprising terlipressin (e.g., a coated capsule or tablet comprising terlipressin), is administered to a subject suffering from hypotension (e.g., neurogenic orthostatic hypotension), once in the morning and once in the afternoon. In another example, the composition comprising terlipressin (e.g., a coated capsule or tablet) comprising terlipressin), is administered to a subject suffering from portal hypertension or bleeding esophageal varices as 2-4 tablets up to 4 times a day.

In some embodiments, the administration occurs on an empty stomach. In some embodiments, the administration occurs prior to food intake (e.g., 1, 2, 3, 4, 6, 8, or more hours prior to food intake). In some embodiments, the administration occurs after food intake (e.g., 1, 2, 3, 4, 6, 8, or more hours after food intake). In some embodiments, the administration occurs during food intake. In some embodiments, the oral administration of terlipressin occurs at least 1 hour before a meal or least 2 hours after a meal, to thereby treat the subject. In some embodiments, the oral administration of terlipressin occurs at least 1 hour before a meal or least 1 hour after a meal, to thereby treat the subject.

In an embodiment, the composition described herein is provided as an oral dosage form. Oral dosages of the present invention, when used for the indicated effects, may be provided in the form of capsules comprising 0.3, 0.5, 1, 1.5, 2, 4, 5, 10, 15, 17, 19, 20, 21, 23, 25, 30, 35, 40, 45, 50 mg or more of therapeutic agent (e.g., terlipressin). In some embodiments, the oral dosage comprising the therapeutic agent (e.g., terlipressin) is a 1, 1.5, 2, 4, 5, 10, 15, 17, 19, 20, 21, 23, 25, 30, 35, 40, 45, 50 mg or more solid dosage form (e.g. capsule or tablet with an enteric coating). In some embodiments, the capsule is a 5, 10, 15, 20, 25, 30, 50 or 100 mg capsule. In some embodiments, the capsule is about 15 to about 25 mg. In some embodiments, the capsule is about 18 to about 22 mg. In some embodiments, the capsule is a 20 mg capsule.

A representative product of the invention is a formulation orally administered as enteric coated-capsules: each capsule contains terlipressin co-lyophilized with a PVP polymer and sodium octanoate, and suspended in a hydrophobic (lipophilic) medium containing: glyceryl tricaprylate, glyceryl monocaprylate, and Tween 80; in another representative product of the invention castor oil is additionally present. The compositions described herein can be administered to a subject i.e. a human or an animal, in order to treat the subject with a pharmacologically or therapeutically effective amount of terlipressin described herein. The animal may be a mammal e g a mouse, rat, pig, dog, horse, cow or sheep.

Compositions of the present invention (e.g., compositions comprising terlipressin) may be administered in a single daily dose, or the total daily dosage may be administered in divided doses of two, three, four, five or six times daily. In some embodiments, the method comprises administration up to 2 times per day. In some embodiments, the composition is administered up to 3 or 4 times per day.

In some embodiments, the composition is administered at a daily dose of from about 1 to about 200 mg/day (e.g., about 1 to about 100 mg/day, about 5 to about 100 mg/day, about 5 to about 50 mg/day), e.g., administered at least 1, 2, 3, or 4 times daily (e.g., in the morning, in the afternoon). In some embodiments, the composition is administered 2 times a day. In some embodiments, the composition is administered 4 times a day. In some embodiments, the composition is administered 3 times a day.

In another example, the composition comprising terlipressin (e.g., a capsule or tablet (e.g., coated capsule or tablet) comprising terlipressin), is administered to a subject suffering from portal hypertension (e.g., bleeding esophageal varices associated with portal hypertension), 1, 2, 3, or 4 times a day. In some embodiments, the subject is administered 1 or 2 tablets or capsules comprising terlipressin 1, 2, 3, or 4 times a day. For example, the subject is administered the composition comprising terlipressin 1 to 2 tablets up to 4 times a day. In some embodiments, the tablet or capsule comprising terlipressin is about 10 to about 30 mg (e.g., about 15 to about 25 mg, about 18 to about 22 mg, about 22 mg) terlipressin. One aspect of this invention is a method for treating a subject suffering from hypotension (e.g. neurogenic orthostatic hypotension or post prandial hypotension), the method comprising administration to the subject of a therapeutically effective amount of oral terlipressin. Another aspect of this invention is a method of treatment of a subject suffering from portal hypertension/bleeding esophageal varices, the method comprising administration to the subject of a therapeutically effective amount of an oral terlipressin in combination with a therapeutically effective amount of at least one liver fibrosis agent. Another aspect of this invention is a unit dosage formulation for oral administration (oral dosage form) comprising a therapeutically effective amount of terlipressin in combination with a therapeutically effective amount of at least one liver fibrosis agent.

Another aspect of this invention is a method for treating a subject suffering from hypotension (e.g. neurogenic orthostatic hypotension or post prandial hypotension), the method comprising administration to the subject of a therapeutically effective amount of oral terlipressin in combination with another drug used for treatment of neurogenic orthostatic hypotension or post prandial hypotension. For example, the drugs to be used in combination with oral terlipressin include mineralocorticoids including but not limited to fludrocortisone. In some embodiments, oral terlipressin is administered in combination with a large volume of physiological liquid (e.g., 100 mL, 200 mL, 500 mL or greater volume of physiological liquid). Thus an aspect of the invention is a method of treating a subject suffering from neurogenic orthostatic hypotension, the method comprising administration to the subject of a therapeutically effective amount of an oral terlipressin in combination with a bolus of water and a therapeutically effective amount of at least one therapeutic agent selected from fludrocortisone, midodrine, pyridostigmine, droxidopa and erythropoietin and/or Northera and/or TD-9855.

Thus an aspect of the invention is a method of treating a subject suffering from post-prandial hypotension, the method comprising administration to the subject of a therapeutically effective amount of an oral terlipressin in combination with a therapeutically effective amount of at least one therapeutic agent selected from guar gum, acabarose and midodrine and optionally in combination with a bolus of water.

Another aspect of this invention is a method for treating a subject suffering from ascites (e.g. caused by liver cirrhosis), the method comprising administration to the subject of a therapeutically effective amount of oral terlipressin in combination with another drug used for treatment of ascites. For example, the drugs to be used in combination with oral terlipressin include albumin, diuretics and/or beta-blockers. An aspect of the invention is a method of treating a subject suffering from ascites, the method comprising administration to the subject of a therapeutically effective amount of an oral terlipressin in combination with a therapeutically effective amount of at least one therapeutic agent selected from a diuretic, a beta-blocker or albumin.

In some embodiments, the methods described herein treat a subject suffering from hypotension (e.g., neurogenic orthostatic hypotension), the method comprising administering one or two doses (e.g., a dose comprising 1 to 2 or more tablets or capsules comprising terlipressin) 15, 20, 30, 40, 45, or 60 minutes before getting up (e.g., in the morning or afternoon; before 4 or 5 pm), for example daily.

In some embodiments, the methods described herein treat a subject suffering from post-prandial hypotension, the method comprising administering one or two doses (e.g., a dose comprising 1 to 2 tablets or capsules comprising terlipressin) 15, 20, 30, 40, 45, or 60 minutes before a meal.

In some embodiments, the tablet or capsule comprising terlipressin is about 10 to about 30 mg (e.g., about 15 to about 25 mg, about 18 to about 22 mg, about 20 mg) terlipressin.

In some embodiments, the methods described herein (e.g., method of orally administering terlipressin) results in reduced side effects relative a method of administering terlipressin by other forms of administration (e.g., intravenous administration). In some embodiments, the methods described herein (e.g., method of orally administering terlipressin) provides greater patient compliance (e.g., compliance by a subject described herein) relative a method of administering terlipressin by other forms of administration (e.g., intravenous administration which is not convenient for domiciliary treatment).

Terlipressin

As described herein, the active pharmaceutical ingredient described herein (e.g., compound described herein, therapeutic agent described herein) is terlipressin, or a pharmaceutically acceptable salt of terlipressin. Terlipressin (also known as triglycyl lysine vasopressin) is a synthetic analogue of the human neuropeptide hormone vasopressin. Terlipressin is a prohormone of lysine-vasopressin (triglycyl lysine vasopressin TGLVP), for example as described in Rittig et al., Movement Disorders, 1991, Vol. 6(1), p 21-28). Following administration and absorption to the circulation, the glycyl residues are cleaved from the prohormone by endothelial peptidases, allowing prolonged release of lysine-vasopressin. Thus terlipressin itself has weak intrinsic vasopressive activity but is transformed to the fully active lysine vasopressin (LVP) by endothelial endopeptidases. Terlipressin is also known by its tradenames Teripress and Glypressin. Terlipressin has a molecular weight of 1227.37 g/mol and is represented by the formula:

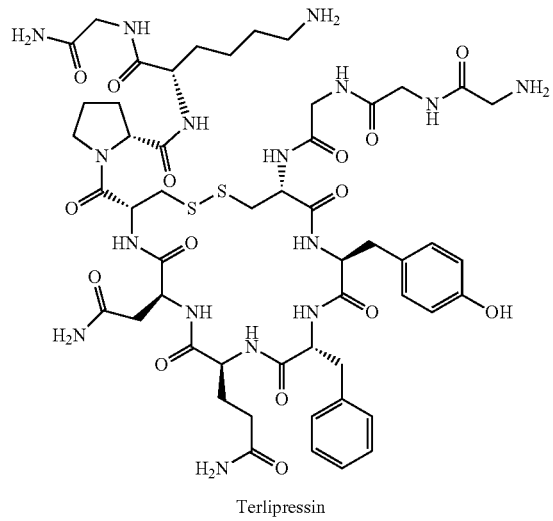 [SMILES: NCCCC[C@H](NC(=O)[C@H]1CCCN1C(=O)[C@@H]1CSSC[C@H](NC(=O)CNC(=O)CNC(=O)CN)C(=O)N[C@@H](Cc2ccc(O)cc2)C(=O)N[C@H](Cc2ccccc2)C(=O)N[C@@H](CCC(N)=O)C(=O)N[C@@H](CC(N)=O)C(=O)N1)C(=O)NCC(N)=O]

Terlipressin

Terlipressin administered intravenously has been used, for example as a vasoactive drug in the management of hypotension (low blood pressure) and for example for treatment of esophageal varices, septic shock, hepatorenal syndrome and ascites.

Pharmaceutical Compositions

The pharmaceutical compositions described herein include terlipressin and a medium chain fatty acid salt in intimate contact or association with a substantially hydrophobic medium. For example, terlipressin and the medium chain fatty acid or derivative thereof may be coated, suspended, sprayed by or immersed in a substantially hydrophobic medium forming a suspension. The compositions of the invention are not emulsions. The compositions are oily suspensions and the amount of water in the compositions is very low, usually 1% or less or 0.5% or less.

The suspension may be a liquid suspension incorporating solid material, or a semi-solid suspension incorporating solid material (an ointment). Many of the compositions described herein comprise a suspension which comprises an admixture of a hydrophobic medium and a solid form wherein the solid form comprises a therapeutically effective amount of terlipressin and at least one salt of a medium chain fatty acid, and wherein the medium chain fatty acid salt is present in the composition at an amount of 10% or more by weight. The solid form may comprise a particle (e.g., consist essentially of particles, or consist of particles). The particle may be produced by lyophilization, by spray drying or by granulation.

The medium chain fatty acid salt may generally facilitate or enhance permeability and/or absorption of terlipressin. In some embodiments, the medium chain fatty acid salts include derivatives of medium chain fatty acid salts. Terlipressin and the medium chain fatty acid salt are in solid form, for example, a solid particle such as a lyophilized particle, granulated particle, pellet or micro-sphere. In preferred embodiments, terlipressin and the medium chain fatty acid salt are both in the same solid form, e.g., both in the same particle. In other embodiments, terlipressin and the medium chain fatty acid salt may each be in a different solid form, e.g. each in a distinct particle.

Unlike emulsions, where water is an essential constituent of the formulation, the compositions described herein provide a solid form such as a particle containing terlipressin, which is then associated with the hydrophobic (oily) medium. The amount of water in the compositions is generally less than 3% by weight, usually less than about 2% or less than 1% by weight or about 0.5% by weight or less.

The compositions described herein are suspensions which comprise an admixture of a hydrophobic medium and a solid form wherein the solid form comprises a therapeutically effective amount of terlipressin and at least one salt of a medium chain fatty acid. The solid form may be a particle (e.g., consist essentially of particles, or consist of particles). The particle may be produced by lyophilization or by spray drying or by granulation. The medium chain fatty acid salt is generally present in the compositions described herein at an amount of 10% or more by weight. In certain embodiments, the medium chain fatty acid salt is present in the composition at an amount of 10%-50%, preferably 11%-18% or about 11%-17% or 12%-16% or 12%-15% or 13%-16% or 13%-15% or 14%-16% or 14%-15% or 15%-16% or most preferably 15% or 16% by weight, and the medium chain fatty acid has a chain length from about 6 to about 14 carbon atoms preferably 8, 9 or 10 carbon atoms.

In some embodiments in the compositions described above, the solid form including terlipressin also includes a stabilizer (e.g., a stabilizer of protein structure). Stabilizers of protein structure are compounds that stabilize protein structure under aqueous or non-aqueous conditions or can reduce or prevent aggregation of terlipressin, for example during a drying process such as lyophilization or other processing step. Stabilizers of structure can be polyanionic molecules, such as phytic acid, polyvalent ions such as Ca, Zn or Mg, saccharides such as a disaccharide (e.g., trehalose, maltose) or an oligo or polysaccharide such as dextrin or dextran, or a sugar alcohol such as mannitol, or an amino acid such as glycine, or polycationic molecules, such as spermine, or surfactants such as polyoxyethylene sorbitan monooleate (Tween 80) or pluronic acid. Uncharged polymers, such as mannitol, methyl cellulose and polyvinyl alcohol, are also suitable stabilizers.

Although polyvinylpyrrolidone (PVP) is known in the art as a stabilizer, in the compositions of the invention described herein, a PVP polymer, for example PVP-12, can serve to increase the effect of the permeability enhancer, e.g., in a synergistic manner Dextran and other matrix forming polymers may have a similar effect as PVP does.

In some embodiments, a bulking agent may be added, for example, mannitol or glycin.

In a particular embodiment of the compositions described herein the salt of the fatty acid is sodium octanoate and the hydrophobic medium is castor oil; in another particular embodiment the composition further comprises glyceryl monooleate and sorbitan monopalmitate or glyceryl monocaprylate and glyceryl tricaprylate and polyoxyethylene sorbitan monooleate; in another particular embodiment the composition further comprises glyceryl tributyrate, lecithin, ethylisovalerate and at least one stabilizer.

An exemplary formulation of terlipressin is as follows:

|  | Ingredient | (% w/w) |
| --- | --- | --- |
| Hydrophilic fraction | Terlipressin | 0.235 |
|  | MgCl$_2$ | 0.000 |
|  | PVP 12 | 10.004 |
|  | Sodium octanoate | 15.015 |
|  | MC 400 | 0.000 |
|  | Water | 1.010 |
| Hydrophobic medium | Span 40 | 0.000 |
|  | Lecithin | 0.000 |
|  | Ethyl isovalerate | 0.000 |
|  | Glyceryl monooleate | 0.000 |
|  | Glyceryl tributyrate | 0.000 |
|  | Castor oil | 0.000 |
|  | Tween 80 | 2.002 |
|  | GMC | 4.004 |
|  | GTC | 67.731 |

Medium Chain Fatty Acid Salt:

The compositions described herein include the salt of a medium chain fatty acid or a derivative thereof in a solid form. For example, the salt of the medium chain fatty acid is in the form of a particle such as a solid particle. In some embodiments, the particle may be characterized as a granulated particle. In at least some embodiments, the solid form may generally result from a spray drying or evaporation process. In preferred embodiments, the salt of the medium chain fatty acid is in the same particle as terlipressin. For example, terlipressin and the salt of the medium chain fatty acid can be prepared together by first preparing a solution such as an aqueous solution comprising both terlipressin and the salt of the medium chain fatty acid and co-lyophilizing the solution to provide a solid form or particle that comprises both terlipressin and the salt of the medium chain fatty acid (and other ingredients). As described above, the resulting solid particles are associated with a hydrophobic medium. For example, the solid particles may be suspended or immersed in a hydrophobic medium.

In different embodiments of the compositions described herein the medium chain fatty acid salt may be in the same particle or in a different particle than that of the API. It is believed that if the medium chain fatty acid salt and terlipressin are dried after solubilization together in the hydrophilic fraction then they are in the same particle in the final powder.

Medium chain fatty acid salts include those having a carbon chain length of from about 6 to about 14 carbon atoms. Examples of fatty acid salts are sodium hexanoate, sodium heptanoate, sodium octanoate (also termed sodium caprylate), sodium nonanoate, sodium decanoate, sodium undecanoate, sodium dodecanoate, sodium tridecanoate, and sodium tetradecanoate. In some embodiments, the medium chain fatty acid salt contains a cation selected from the group consisting of potassium, lithium, ammonium and other monovalent cations e.g. the medium chain fatty acid salt is selected from lithium octanoate or potassium octanoate or arginine octanoate or other monovalent salts of the medium chain fatty acids.

In general, the amount of medium chain fatty acid salt in the compositions described herein may be from 10% up to about 50% by weight of the bulk pharmaceutical composition. For example, the medium chain fatty acid salt may be present at an amount of about 10%-50%, preferably about 11%-40% most preferably about 11%-28% by weight for example at about 12%-13%, 13%-14%, 14%-15%, 15%-16%, 16%-17%, 17%-18%, 18%-19%, 19%-20%, 20%-21%, 21%-22%, 22%-23%, 23%-24%, 24%-25%, 25%-26%, 26%-27%, or 27%-28% by weight of the bulk pharmaceutical composition. In other embodiments the medium chain fatty acid salt may be present at an amount of at least about 11%, at least about 12%, at least about 13%, at least about 14%, at least about 15% at least about 16%, at least about 17%, at least about 18%, at least about 19%, at least about 20%, at least about 21%, at least about 22%, at least about 23%, at least about 24%, at least about 25%, at least about 26%, at least about 27% or at least about 28% by weight of the bulk pharmaceutical composition. In specific embodiments, the medium chain fatty acid salt (sodium, potassium, lithium or ammonium salt or a mixture thereof) is present at about 12%-21% by weight of the bulk pharmaceutical composition preferably 11%-18% or about 11%-17% or 12%-16% or 12%-15% or 13%-16% or 13%-15% or 14%-16% or 14%-15% or 15%-16% or most preferably 15% or 16%. In specific embodiments, the medium chain fatty acid salt (having a carbon chain length of from about 6 to about 14 carbon atoms particularly 8, 9 or 10 carbon atoms) is present at about 12%-21% by weight of the bulk pharmaceutical composition preferably 11%-18% about 11%-17% or 12%-16% or 12%-15% or 13%-16% or 13%45% or 14%-16% or 14%45% or 15%-16% or most preferably 15% or 16%. In specific embodiments the medium chain fatty acid salt (for example salts of octanoic acid, salts of suberic acid, salts of geranic acid) is present at about 12%-21% by weight of the bulk pharmaceutical composition preferably 11%-18% about 11%-17% or 12%-16% or 12%-15% or 13%-16% or 13%-15% or 14%-16% or 14%-15% or 15%-16% or most preferably 15% or 16%. In certain embodiments, the medium chain fatty acid salt is present in the solid powder at an amount of 50% to 90%, preferably at an amount of 70% to 80%.

One embodiment of the invention comprises a composition comprising a suspension which consists essentially of an admixture of a hydrophobic medium and a solid form wherein the solid form comprises a therapeutically effective amount terlipressin and at least one salt of a medium chain fatty acid, and wherein the medium chain fatty acid salt is not a sodium salt. The salt may be the salt of another cation e.g. lithium, potassium or ammonium; an ammonium salt is preferred.

Matrix Forming Polymer:

In certain embodiments the composition of the invention comprises a suspension which comprises an admixture of a hydrophobic medium and a solid form wherein the solid form comprises a therapeutically effective amount of terlipressin, at least one salt of a medium chain fatty acid and a matrix forming polymer, and wherein the matrix forming polymer is present in the composition at an amount of 3% or more by weight. In certain embodiments the composition comprises a suspension which consists essentially of an admixture of a hydrophobic medium and a solid form wherein the solid form comprises a therapeutically effective amount of terlipressin, at least one salt of a medium chain fatty acid and a matrix forming polymer, and wherein the matrix forming polymer is present in the composition at an amount of 3% or more by weight. In particular embodiments the matrix forming polymer is dextran or a polyvinylpyrrolidone polymer (PVP), obtainable in various molecular weights from BASF. In particular embodiments the polyvinylpyrrolidone is present in the composition at an amount of about 2% to about 20% by weight, preferably at an amount of about 3% to about 18% by weight, more preferably at an amount of about 5% to about 15% by weight, most preferably at an amount of about 10% by weight. In certain particular embodiments the polyvinylpyrrolidone is PVP-12 and/or has a molecular weight of about 3000. Other matrix forming polymers have a similar effect in the compositions of the invention; such matrix forming polymers include ionic polysaccharides (for example alginic acid and alginates) or neutral polysaccharides (for example dextran and HPMC), polyacrylic acid and poly methacrylic acid derivatives and high molecular weight organic alcohols (for example polyvinyl alcohol).

Hydrophilic Fraction:

In embodiments of the invention, the above compounds, including terlipressin and the medium chain fatty acid salt are solubilized in an aqueous medium and then dried to produce a powder. The drying process may be achieved for example by lyophilization or spray drying or granulation. The powder obtained is termed the "hydrophilic fraction". In the hydrophilic fraction water is normally present at an amount of less than 6% or less than 3% or about 2% or less.

Lyophilization may be carried out by methods known in the art e.g. as described in *Lyophilization: Introduction and Basic Principles*, Thomas Jennings, published by Interpharm/CRC Press Ltd (1999, 2002) The lyophilizate may optionally be milled (e.g. below 150 micron) or ground in a mortar. During industrial production the lyophilizate is preferably milled before mixing of the hydrophilic fraction and the hydrophobic medium in order to produce batch-to-batch reproducibility.

Spray drying may be carried out by methods known in the art e.g. as described by Walters et al (2014) *Next Generation Drying Technologies for Pharmaceutical Applications*, J. of Pharm Sci 103; 2673-2695

Granulation may be carried out as shown by methods known in the art e.g. as described in *Granulation*, Salman et al, eds, Elsevier (2006) and in *Handbook of Pharmaceutical Granulation Technology*, $2^{nd}$ edition, (2005) Dilip M. Parikh, ed. Various binders may be used in the granulation process such as celluloses (including microcrystalline celluloses), lactoses (e.g., lactose monohydrate), dextroses, starch and mannitol and other binders as described in the previous two references.

Hydrophobic Medium:

Oil:

As described above, in the compositions of the invention described herein terlipressin and the medium chain fatty acid salt are in intimate contact or association with a hydrophobic medium. For example, one or both may be coated, suspended, immersed or otherwise in association with a hydrophobic medium. Suitable hydrophobic mediums can contain, for example, aliphatic, cyclic or aromatic molecules. Examples of a suitable aliphatic hydrophobic medium include, but are not limited to, mineral oil, fatty acid monoglycerides, diglycerides, triglycerides, ethers, esters, and combinations thereof. Examples of a suitable fatty acid are octanoic acid, decanoic acid and dodecanoic acid, also C7 and C9 fatty acids and di-acidic acids such as sebacic acid and suberic acid, and derivatives thereof. Examples of triglycerides include, but are not limited to, long chain triglycerides, medium chain triglycerides, and short chain triglycerides. For example, the long chain triglyceride can be castor oil or coconut oil or olive oil, and the short chain triglyceride can be glyceryl tributyrate and the medium chain triglyceride can be glyceryl tricaprylate. Monoglycerides are considered to be surfactants and are described below. Exemplary esters include ethyl isovalerate and butyl acetate. Examples of a suitable cyclic hydrophobic medium include, but are not limited to, terpenoids, cholesterol, cholesterol derivatives (e.g., cholesterol sulfate), and cholesterol esters of fatty acids. A non-limiting example of an aromatic hydrophobic medium includes benzyl benzoate.

In some embodiments of the compositions described herein, it is desirable that the hydrophobic medium include a plurality of hydrophobic molecules. In some embodiments of the compositions described herein the hydrophobic medium also includes one or more surfactants (see below).

In some embodiments of the compositions described herein, the hydrophobic medium also includes one or more adhesive polymers such as methylcellulose, ethylcellulose, hydroxypropylmethylcellulose (HPMC), or poly(acrylate) derivative Carbopol®934P (C934P). Such adhesive polymers may assist in the consolidation of the formulation and/or help its adherence to mucosal surfaces.

Surface Active Agents (Surfactants):

The compositions of this invention described herein can further include a surface-active agent. For example, the surface-active agent can be a component of the hydrophobic medium as described above, and/or the surface-active agent can be a component of a solid form as described above, for example in the solid form or particle that includes terlipressin.

Suitable surface-active agents include ionic and non-ionic surfactants. Examples of ionic surfactants are lecithin (phosphatidyl choline), bile salts and detergents. Examples of non-ionic surfactants include monoglycerides, cremophore, a polyethylene glycol fatty alcohol ether, a sorbitan fatty acid ester, a polyoxyethylene sorbitan fatty acid ester, Solutol HS15, or a poloxamer or a combination thereof. Examples of monoglycerides are glyceryl monocaprylate (also termed glyceryl monooctanoate), glyceryl monodecanoate, glyceryl monolaurate, glyceryl monomyristate, glyceryl monostearate, glyceryl monopalmitate, and glyceryl monooleate. Examples of sorbitan fatty acid esters include sorbitan monolaurate, sorbitan monooleate, and sorbitan monopalmitate (Span 40), or a combination thereof. Examples of polyoxyethylene sorbitan fatty acid esters include polyoxyethylene sorbitan monooleate (Tween 80), polyoxyethylene sorbitan monostearate, polyoxyethylene sorbitan monopalmitate or a combination thereof. The commercial preparations of monoglycerides that were used also contain various amounts of diglycerides and triglycerides.

Compositions described herein including a surface-active agent generally include less than about 12% by weight of total surface active agent (e.g., less than about 10%, less than about 8%, less than about 6%, less than about 4%, less than about 2%, or less than about 1%). In particular embodiments of the invention the total sum of all the surfactants is about 6%.

Methods of Making Pharmaceutical Compositions and the Compositions Produced

Also included in the invention are methods of producing the compositions described herein. Thus one embodiment of the invention is a process for producing a pharmaceutical composition which comprises preparing a water-soluble composition comprising a therapeutically effective amount of terlipressin and a medium chain fatty acid salt (as described above), drying the water soluble composition to obtain a solid powder, and suspending the solid powder in a hydrophobic medium, to produce a suspension containing in solid form terlipressin and the medium chain fatty acid salt, thereby producing the pharmaceutical composition, wherein the pharmaceutical composition contains 10% or more by weight of medium chain fatty acid salt.

One embodiment is a process for producing a pharmaceutical composition which comprises providing a solid powder of a therapeutically effective amount terlipressin and a solid powder comprising a medium chain fatty acid salt, and suspending the solid powders in a hydrophobic medium, to produce a suspension containing in solid form terlipressin and the medium chain fatty acid salt, thereby producing the pharmaceutical composition, wherein the pharmaceutical composition contains 10% or more by weight of medium chain fatty acid salt.

In one embodiment of the processes and compositions described herein, the water-soluble composition is an aqueous solution. In certain embodiments, the drying of the water-soluble composition is achieved by lyophilization (freeze-drying), spray-drying or by granulation. In certain embodiments, the drying step removes sufficient water so that the water content in the bulk pharmaceutical composition is lower than about 6% by weight, about 5% by weight, about 4% by weight, about 3% or about 2% or about 1% or about 0.5% or less by weight. In certain embodiments of the processes and compositions described herein the drying step removes an amount of water so that the water content in the solid powder is lower than 6% or 5% or 4% or 3% or preferably lower than 2% by weight. The water content is normally low and the water may be adsorbed to the solid phase during lyophilization i.e. the water may be retained by intermolecular bonds. In certain embodiments, the water-soluble composition additionally comprises a stabilizer for example methyl cellulose. In preferred embodiments of the processes and compositions described herein the hydrophobic medium is castor oil or glyceryl tricaprylate or glyceryl tributyrate or a combination thereof and may additionally contain octanoic acid; in certain embodiments the hydrophobic medium comprises an aliphatic, olefinic, cyclic or aromatic compound, a mineral oil, a paraffin, a fatty acid such as octanoic acid, a monoglyceride, a diglyceride, a triglyceride, an ether or an ester, or a combination thereof. In certain embodiments of the processes and compositions described herein the triglyceride is a long chain triglyceride, a medium chain triglyceride preferably glyceryl tricaprylate or a short chain triglyceride preferably glyceryl tributyrate, and the long chain triglyceride is castor oil or coconut oil or a combination thereof. In certain embodiments of the processes and compositions described herein the hydrophobic medium comprises castor oil or glyceryl tricaprylate or glyceryl tributyrate or a combination or mixture thereof, and may additionally comprise octanoic acid. In certain embodiments of the processes and compositions described herein the hydrophobic medium comprises glyceryl tricaprylate or a low molecular weight ester for example ethyl isovalerate or butyl acetate. In certain embodiments of the processes and compositions described herein the main component by weight of the hydrophobic medium is castor oil and may additionally comprise glyceryl tricaprylate. In certain embodiments of the processes and compositions described herein the main component by weight of the hydrophobic medium is glyceryl tricaprylate and may additionally comprise castor oil.

In certain embodiments, the composition comprises a suspension which consists essentially of an admixture of a hydrophobic medium and a solid form wherein the solid form comprises a therapeutically effective amount of terlipressin and at least one salt of a medium chain fatty acid, and wherein the medium chain fatty acid salt is present in the composition at an amount of 10% or more by weight. In certain embodiments, the hydrophobic medium consists essentially of castor oil, glyceryl monooleate and glyceryl tributyrate; or the hydrophobic medium consists essentially of glyceryl tricaprylate and glyceryl monocaprylate; or the hydrophobic medium consists essentially of castor oil, glyceryl tricaprylate and glyceryl monocaprylate. In certain embodiments, the hydrophobic medium comprises a triglyceride and a monoglyceride and in certain particular embodiments the monoglyceride has the same fatty acid radical as the triglyceride. In certain of these embodiments the triglyceride is glyceryl tricaprylate and the monoglyceride is glyceryl monocaprylate. In certain embodiments, the medium chain fatty acid salt in the water-soluble composition has the same fatty acid radical as the medium chain monoglyceride or as the medium chain triglyceride or a combination thereof. In certain of these embodiments the medium chain fatty acid salt is sodium caprylate (sodium octanoate) and the monoglyceride is glyceryl monocaprylate and the triglyceride is glyceryl tricaprylate.

Many of the compositions described herein comprise a suspension which comprises an admixture of a hydrophobic medium and a solid form wherein the solid form comprises a therapeutically effective amount of terlipressin and at least one salt of a medium chain fatty acid, and wherein the medium chain fatty acid salt is present in the composition preferably at an amount of 10% or more by weight. The solid form may be a particle (e.g., consist essentially of particles, or consists of particles). The particle may be produced by lyophilization or by granulation or by spray drying. In one embodiment the formulation consists essentially of or comprises a suspension which comprises an admixture of a hydrophobic medium and a solid form wherein the solid form comprises a therapeutically effective amount of terlipressin and about 10-20% preferably 15% medium chain fatty acid salt preferably sodium octanoate and a polyvinylpyrrolidone polymer; and wherein the hydrophobic medium comprises about 20-80%, preferably 30-70% medium or short chain triglyceride preferably glyceryl tricaprylate or glyceryl tributyrate, about 0-50% preferably 0-30% castor oil, about 3-10% surfactants, preferably about 6%, preferably glyceryl monocaprylate and Tween 80; in particular embodiments terlipressin is present at an amount of less than 33%, or less than 25%, or less than 10%, or less than 3% or less than 2%.

In the above formulations, the percentages are weight/weight.

Under normal storage conditions, terlipressin, within the formulations of the invention, is stable over an extended period of time. The chemical and physical state of the formulation is stable. Once administered to the intestine, terlipressin is protected from damage by the GI environment since the formulations are oil-based and therefore a separate local environment is created in the intestine where terlipressin is contained in particles suspended in oil which confers stability in vivo.

In certain embodiments, the process produces a composition which consists essentially of terlipressin and a medium chain fatty acid salt and a hydrophobic medium. In embodiments of the invention the solid powder (solid form) consists essentially of terlipressin and a medium chain fatty acid salt. Further embodiments of the invention are pharmaceutical compositions produced by the process describe herein. Particular embodiments of the invention comprise an oral dosage form comprising the pharmaceutical composition, in particular an oral dosage form which is enteric coated. Further embodiments of the invention comprise a capsule containing the compositions of the invention, and in various embodiments the capsule is a hard gel or a soft gel capsule, and generally the capsule is enteric-coated. Other embodiments of the invention comprise a rectal dosage form comprising the pharmaceutical composition, in particular a suppository, or a buccal dosage form. A kit comprising instructions and the dosage form is also envisaged.

Terlipressin and/or medium chain fatty acid salt, or any combination of terlipressin and other components, such as protein stabilizers, can be prepared in a solution of a mixture (e.g., forming an aqueous solution or mixture) which can be lyophilized together and then suspended in a hydrophobic medium. Other components of the composition can also be optionally lyophilized or added during reconstitution of the solid materials.

In some embodiments, terlipressin is solubilized in a mixture, for example, including one or more additional components such as a medium chain fatty acid salt, a stabilizer and/or a surface-active agent, and the solvent is removed to provide a resulting solid powder (solid form), which is suspended in a hydrophobic medium. In some embodiments, terlipressin and/or the medium chain fatty acid salt may be formed into a granulated particle that is then associated with the hydrophobic medium (for example suspended in the hydrophobic medium or coated with the hydrophobic medium). If desired, the pharmaceutical composition may also contain minor amounts of non-toxic auxiliary substances such pH buffering agents, and other substances such as for example, sodium acetate and triethanolamine oleate.

In some embodiments, the solid form may be a particle (e.g., consist essentially of particles, or consists of particles). In some embodiments, the particle may be produced by lyophilization, by spray drying or by granulation. In some embodiments of this process the fatty acid salt is sodium octanoate; in further embodiments of this process the medium chain fatty acid salt is present in the composition at an amount of about 11% to about 40% by weight or at an amount of about 11% to about 28% by weight or at an amount of about 15% by weight. In some embodiments of this process the composition additionally comprises a matrix forming polymer and in particular embodiments of this process the matrix forming polymer is dextran or a polyvinylpyrrolidone polymer (PVP); in further embodiments of this process the polyvinylpyrrolidone is present in the composition at an amount of about 2% to about 20% by weight or at an amount of about 4% to about 15% by weight, or at an amount of about 10% by weight. In certain embodiments of this process the polyvinylpyrrolidone polymer is PVP-12 and/or has a molecular weight of about 3000. The composition may in addition include surfactants as described above. The solid form may also contain a binder. There also may be small quantities of other hydrophobic constituents as described above. The pharmaceutical products of these processes are further embodiments of the invention.

Capsules:

Preferred pharmaceutical compositions are oral dosage forms or suppositories. Exemplary dosage forms include gelatin or vegetarian capsules like starch hydroxypropylmethyl cellulose ("HPMC") capsules, enteric coated, containing the bulk drug product. Capsules which may be used to encapsulate the compositions of this invention are known in the art and are described for example in *Pharmaceutical Capsules* edited by Podczech and Jones, Pharmaceutical Press (2004) and in *Hard gelatin capsules today-and tomorrow*, 2nd edition, Steggeman ed published by Capsugel Library (2002).

Tablets:

Pharmaceutical compositions described herein may also be configured as a tablet. Tablets may be made by compression or molding, optionally with one or more ingredients. Compressed tablets may be prepared using binder (for example, gelatin or hydroxypropylmethyl cellulose), lubricant, inert diluent, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Additional Formulations:

The compositions of the invention may be formulated using additional methods known in the art, for example as described in the following publications: *Pharmaceutical Dosage Forms* Vols 1-3 ed. Lieberman, Lachman and Schwartz, published by Marcel Dekker Inc, New York (1989); *Water-insoluble Drug Formulation* $2^{nd}$ edition, Liu, editor, published by CRC Press, Taylor and Francis Group (2008); *Therapeutic Peptides and Proteins: Formulation, Processing and Delivery Systems*, $2^{nd}$ edition by Ajay K. Banga (author) published by CRC Press, Taylor and Francis Group (2006); *Protein Formulation and Delivery*, $2^{nd}$ edition, McNally and Hasted eds, published by Informa Healthcare USA Inc (2008); and *Advanced Drug Formulation to Optimize Therapeutic Outcomes*, Williams et al eds, published by Informa Healthcare USA (2008).

The compositions of the invention may be formulated using microparticulate technology for example as described in *Microparticulate Oral Drug Delivery*, Gerbre-Selassie ed., published by Marcel Dekker Inc (1994) and in Dey et al, *Multiparticulate Drug Delivery Systems for Controlled Release*, Tropical Journal of Pharmaceutical Research, September 2008; 7 (3): 1067-1075.

Kits

Oral dosage forms may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Definitions

As used herein the term "pharmacologically or therapeutically effective amount" means that amount of a drug or pharmaceutical agent (e.g. terlipressin) that will elicit the biological or medical response of a tissue, system, animal or human that is being sought by a researcher or clinician and/or halts or reduces the progress of the condition being treated or which otherwise completely or partly cures or acts palliatively on the condition described herein or prevents development of the condition described herein (e.g., hypotension for example neurogenic orthostatic hypotension or postprandial hypotension; portal hypertension for example bleeding esophageal varices associated with portal hypertension) or ascites for example associated with liver cirrhosis.

Administered "in combination", as used herein, means that two (or more) different therapeutic agents are delivered to the subject during the course of the subject's affliction with the disorder, e.g., the two or more therapeutic agents are delivered after the subject has been diagnosed with the disorder and before the disorder has been cured or eliminated or treatment has ceased for other reasons. In some embodiments, the delivery of one therapeutic agent is still occurring when the delivery of the second begins, so that there is overlap in terms of administration. This is sometimes referred to herein as "simultaneous" or "concurrent delivery". In other embodiments, the delivery of one therapeutic agent ends before the delivery of the other treatment begins. In some embodiments of either case, the therapeutic agents are more effective because of combined administration. For example, the second therapeutic agent is more effective, e.g., an equivalent effect is seen with less of the second therapeutic agent, or the second therapeutic agent reduces symptoms and side-effects to a greater extent, than would be seen if the second therapeutic agent were administered in the absence of the first therapeutic agent, or the analogous situation is seen with the first therapeutic agent. In some embodiments, delivery is such that the reduction in a symptom, or other parameter related to the disorder is greater than what would be observed with one therapeutic agent delivered in the absence of the other. The effect of the two therapeutic agents can be partially additive, wholly additive, or greater than additive. The delivery can be such that an effect of the first therapeutic agent delivered is still detectable when the second is delivered.

As used herein, the term "treatment" as for example in "method of treatment" or "treat" or "treating" refers to therapeutic treatment, wherein the object is to reduce or reverse or prevent the symptoms or side-effects of a disease or disorder. In some embodiments, the compounds or compositions disclosed herein are administered prior to onset of the disease or disorder. In some embodiments, the compounds or compositions disclosed herein are during or subsequent to the onset of the disease or disorder.

As used herein the term "therapy reducing liver fibrosis agent" and the term "liver fibrosis agent" are used interchangeably. A liver fibrosis agent is a drug used for treatment of liver fibrosis and/or non-alcoholic steatohepatitis (NASH) and/or primary biliary cirrhosis. Such liver fibrosis agents (drugs) to be used in combination with oral terlipressin include pirfenidone, nintedanib, obeticholic acid, urodeoxycholic acid, emricasan, vitamin E, pioglitazone, liraglutide, pentoxifylline and metformin. The agents pioglitazone, liraglutide, pentoxifylline and metformin are particularly used for treatment of NASH.

The function and advantages of these and other embodiments will be more fully understood from the following examples. These examples are intended to be illustrative in nature and are not to be considered as limiting the scope of the systems and methods discussed herein.

EXAMPLES

Example 1. Bioavailability of Terlipressin in Dogs

Terlipressin (tradename Glypressin, Ferring) was administered to one group of six dogs via intravenous (IV) administration and terlipressin (BCN Peptides) in the proprietary formulation below (Table 1) was administered to another group of six dogs via oral administration as enteric-coated capsules. The IV dosage was 0.2 mg per dog which is similar to the therapeutic dosage in humans. The oral dosage was 20 mg, and was selected by assuming a BA of about 1%. The concentration of both terlipressin and the active metabolite lysine vasopressin are shown as a function of time. The pharmacokinetic parameters of the active metabolite lysine-vasopressin were determined as well as terlipressin. Each Glypressin ampule contains 1 mg terlipressin acetate, which is equivalent to 0.85 mg terlipressin base. All doses in this study are expressed on the basis of terlipressin base.

All animals were fasted for at least 12 hours prior to dosing and through the first 4 hours of blood sample collection.

In the oral terlipressin capsule treatments, in order to acidify the stomach of the dog, approximately 30 minutes prior to dosing each animal received a single subcutaneous (SC) injection of pentagastrin (0.12 mg/mL) at a dose level of 0.006 mg/kg and a dose volume of 0.05 mL/kg. The same dogs can be used for more than one treatment, with a wash-out period of at least 1 week.

Blood was withdrawn at pre-determined times as follows:

IV: pre-dose, 0.083, 0.166, 0.33, 0.66, 1, 1.5, 2, 3, 4, 5, 6, and 9 hours post-dose.

Oral capsule: pre-dose, 0.5, 1, 1.5, 2, 2.5, 3, 3.5, 4, 4.5, 5.5, 6.5, 7.5, 9 and 12 hours post-dose.

Results are shown for the intravenous administration group in FIG. 1A and for the oral administration group in FIG. 1B and also are shown in Table 2 below.

TABLE 1 below provides the composition comprising terlipressin as used in this dog study. The formulation comprises 10% PVP and 15% sodium octanoate in the hydrophilic fraction, and contains glyceryl tricaprylate as the main constituent of the hydrophobic medium.

TABLE 1

Formulation Comprising Terlipressin
The formulation used in the dog study is as follows:

| | Ingredient | % wt/wt |
|---|---|---|
| Hydrophilic fraction | Terlipressin (free base) | 1.67 |
| | PVP-12 | 10 |
| | $MgCl_2$ | 0.6 |
| | Sodium caprylate | 15 |
| Hydrophobic medium | GMC | 4.0 |
| | GTC | 67 |
| | Tween 80 | 2 |

TABLE 2 below shows the Cmax, AUC, and half time for terlipressin administered IV ("IV terlipressin") and orally ("Oral terlipressin") in this study.

TABLE 2

Bioavailability of Terlipressin and Vasopressin in Dogs

| | Administered | | | |
|---|---|---|---|---|
| | IV terlipressin 0.2 mg (n = 6) | Oral terlipressin 20 mg (n = 4) | IV terlipressin 0.2 mg (n = 6) | Oral terlipressin 20 mg (n = 6) |
| Measured | Plasma terlipressin | | Plasma vasopressin (active metabolite) | |
| Cmax (pg/mL) | 59,130 ± 30,875 | 22,705 ± 22,255 | 1,286 ± 599 | 2,921 ± 2,984 |
| $AUC_{(0-t)}$ (hxpg/mL) | 9,133 ± 4.282 | 13,319 ± 11,282 | 1,693 ± 579 | 3,499 ± 3,757 |
| $AUC_{(inf)}$ (hxpg/mL) | 9,138 ± 4,280 | 13,334 ± 11,284 | 1,696 ± 579 | 3,504 ± 3,759 |
| T½ (h) | 0.232 ± 0.022 | 0.61 ± 0.24 | 0.68 ± 0.11 | 0.84 ± 0.41 |

Note:
In the above Table, $AUC_{0-t}$ (hxpg/mL) was calculated by standard methods; AUC = area under curve, h = hour and t (time) = 9 h for IV and t = 12 h for oral. $AUC_{(inf)}$ (hxpg/mL) where inf = infinity was calculated by standard methods of extrapolation.

These results demonstrate that orally administered terlipressin produces blood (plasma) levels which are similar to the therapeutic dose.

Example 2. Oral Terlipressin for Treatment of Neurogenic Orthostatic Hypotension Patients with neurogenic orthostatic hypotension are randomly assigned to be treated with oral terlipressin (for example up to 100 mg daily administered twice daily) or placebo, in addition to standard of care. The patient has to be fasting for at least two hours prior to start of the study. Blood pressure and heart rate are measured in the supine position before and after oral administration of terlipressin or placebo. After 40 mins in the supine position the patients are tilted head up to 45° for 20 minutes, at which point the blood pressure and heart rate are measured again Primary Outcome Measures:
  Change over baseline of blood pressure.
Secondary Outcome Measures:
  Measurement of dizziness, lightheadedness, syncope (fainting), fatigue, blurry vision, weakness in the tilt position.

Example 3. Oral Terlipressin for Treatment of Ascites

Patients that are confirmed to have ascites, for example ascites associated with liver disease such as liver cirrhosis (e.g., liver cirrhosis without type 1 or type 2 HRS), hepatorenal syndrome (HRS) (e.g., type 1 or type 2 HRS), heart disease (e.g. heart failure) or malignant ascites are orally administered terlipressin for example up to 100 mg daily administered twice daily over the course of treatment ranging from 1 day to 28 days. The patient must take the drug at least one hour before a meal or at least two hours after a meal.

Primary Outcome Measures:

A decrease in the severity of ascites and the accumulation of ascites fluid compared to the 28-day period prior to treatment. This method is also expected to reduce the number of paracentesis procedures required to remove ascitic fluid over a 28-day period, compared to the 28-day period prior to treatment inception, and some patients may avoid paracentesis altogether. Additionally, the average amount of fluid withdrawn after beginning oral terlipressin therapy is expected to be significantly less than prior to the start of treatment.

Secondary Outcome Measures:

Improvement in patient health status (achieved safely with no serious side effects) compared to the 28-day period prior to treatment inception.

Example 4. Oral Terlipressin for Secondary Prevention of Esophageal Variceal Hemorrhage The purpose of this clinical trial is to study the efficacy of beta blocker (e.g., propranolol) versus oral terlipressin in the prevention of esophageal variceal re-bleeding and improvement in survival.

Patients that have had an episode of esophageal bleeding are randomized to receive beta blocker (e.g., propranolol) or oral terlipressin.

The beta blocker propanol is administered as known in the art e.g., propranolol is started at a dose of 20 mg twice daily. The principle of incremental dosing is used to achieve the target heart rate for propranolol. The dose is increased every alternate day to achieve a target heart rate of 55/min or to the maximal dose to 360 mg/day if the medication was well tolerated and the systolic blood pressure was >90 mm Hg. On the occurrence of intolerable adverse effects, systolic blood pressure <90 mm Hg or pulse rate <55/min, the dose of the medication is decreased step-wise, and eventually stopped if these adverse events persist.

The terlipressin is administered orally at the dosage of one to four capsules (20 mg each) per day, preferably one hour before a meal or two hours after a meal.

Primary Outcome Measures:

Re-bleeding from esophageal varices or death [Time Frame: One year].

Secondary Outcome Measures:

Increase or decrease in the size of esophageal varices, appearance of new esophageal varices and appearance or worsening of portal hypertensive gastropathy and complications. [Time Frame: One year]

Example 5. Oral Terlipressin for Treatment of Post-Prandial Hypotension

Patients with post-prandial hypotension are randomly assigned to two groups—one to be treated with oral terlipressin (for example up to 100 mg, administered to a fasting patient one hour prior to a Meal Test) and the other to be treated with placebo; a third group can comprise patients receiving standard of care.

Tests administered before and after a standard meal in all groups:

Heart rate [Time Frame: continuously during Meal Test; about 4 hours].

Heart rate is measured continuously one hour prior to and during the Meal Tests. Each Meal Test takes approximately 4 hours.

Blood pressure [Time Frame: One hour prior to and continuously during Meal Tests (approximately 4 hours)].

Blood pressure is measured continuously during each of the Meal Tests (approximately 4 hours).

Middle cerebral artery velocity [Time Frame: continuously during Meal Tests (approximately 4 hours)].

Middle cerebral artery velocity is measured continuously e.g., by transcranial doppler one hour prior to and during the Meal Tests (approximately 4 hours).

Serum glucose [Time Frame: One hour prior to and every 15 minutes during Meal Tests].

Serum glucose is measured one hour prior to and every 15 minutes during Meal Tests.

Serum insulin [Time Frame: Every 15 minutes during Meal Tests (approximately 4 hours)].

Serum insulin levels are collected every 15 minutes during the Meal Tests (approximately 4 hours).

Serum peptides: GIP (gastric inhibitory polypeptide) and GLP-1 (glucagon like peptide) [Time Frame: Every 15 minutes during Meal Tests (approximately 4 hours)].

Serum peptides are collected every 15 minutes for the duration of the Meal Tests (approximately 4 hours).

Catecholamines [Time Frame: Continuously during Meal Test (approximately 4 hours)]

Catecholamine levels are collected continuously during the Meal Tests (approximately 4 hours).

Primary Outcome Measures:

Blood pressure changes between the pre- and post-prandial measurements and difference (improvement) in those changes between terlipressin and the two other groups.

Secondary Outcome Measures:

Measurement of post-prandial dizziness, lightheadedness, syncope (fainting), fatigue, blurry vision and weakness.

The invention claimed is:

1. A method of treating a subject suffering from ascites, the method comprising orally administering to the subject a pharmaceutical composition configured as a tablet or capsule, wherein the pharmaceutical composition comprises a therapeutically effective amount of terlipressin or a pharmaceutically acceptable salt thereof, thereby treating the subject.

2. The method of claim 1, wherein the tablet or capsule is administered 1, 2, 3 or 4 times daily.

3. The method of claim 1, wherein the tablet or capsule comprises 5 to 30 mg terlipressin or a pharmaceutically acceptable salt thereof.

4. The method of claim 1, wherein the subject is administered 5 to 100 mg terlipressin daily.

5. The method of claim 1, wherein the terlipressin is administered for about one day to about 12 months.

6. The method of claim 1, wherein the terlipressin dose escalates over about one day to about 12 months.

7. The method of claim 1, wherein the method results in reduced side effects relative to a method of administering terlipressin by other forms of administration.

8. The method of claim 1, wherein the ascites is associated with liver cirrhosis.

9. The method of claim 8, wherein the terlipressin is administered in combination with a diuretic, albumin, a beta blocker, or a vasopressin V2-receptor antagonist (vaptan).

10. The method of claim 4, wherein the subject is administered 20 to 100 mg terlipressin daily.

11. The method of claim 10, wherein the subject is administered 40 to 100 mg terlipressin daily.

12. The method of claim 10, wherein the subject is administered 60 to 100 mg terlipressin daily.

13. The method of claim 10, wherein the subject is administered 80 mg terlipressin daily.

* * * * *